(12) United States Patent
Wang et al.

(10) Patent No.: US 7,598,379 B2
(45) Date of Patent: Oct. 6, 2009

(54) METHODS FOR THE SYNTHESIS OF UNSYMMETRICAL CYCLOALKYL SUBSTITUTED XANTHINES

(75) Inventors: Guoquan Wang, Charlottesville, VA (US); Jayson M. Rieger, Charlottesville, VA (US); Robert D. Thompson, Charlottesville, VA (US)

(73) Assignee: PGx Health, LLC, Newton, MA (US)

( * ) Notice: Subject to any disclaimer, the term of this patent is extended or adjusted under 35 U.S.C. 154(b) by 456 days.

(21) Appl. No.: 11/362,390

(22) Filed: Feb. 27, 2006

(65) Prior Publication Data

US 2007/0105821 A1 May 10, 2007

Related U.S. Application Data

(60) Provisional application No. 60/656,104, filed on Feb. 25, 2005.

(51) Int. Cl.
*C07D 473/06* (2006.01)
*C07D 473/04* (2006.01)
*C07D 239/545* (2006.01)
*C07D 401/12* (2006.01)

(52) U.S. Cl. .................. 544/269; 544/268; 544/270; 544/273; 544/310; 544/311; 544/312

(58) Field of Classification Search ............. 544/268, 544/269, 270, 273
See application file for complete search history.

(56) References Cited

U.S. PATENT DOCUMENTS

| 4,081,455 | A | * | 3/1978 | Kuhla | ............. | 540/304 |
| 4,138,433 | A | * | 2/1979 | Kleiner et al. | ............. | 562/876 |
| 5,447,933 | A | * | 9/1995 | Suzuki et al. | ............. | 514/263.34 |
| 5,675,005 | A | * | 10/1997 | Kufner-Muhl et al. | ......... | 544/271 |

OTHER PUBLICATIONS

Jacobson et al, Journal of Medicinal Chemistry (1989), 32(8), 1873-9.*
Turner, "The Design of Organic Synthesis" (Elsevier, 1976), pp. 10 and 149.*
Mayer et al., Chem Soc. Rev., 30, 332 (2001).*
Chen et al., Angewandte Chemie Int. Ed. vol. 37, Issue 1/2, pp. 91-93 (1998).*
Science 310, p. 409 (Oct. 21, 2005).*
Jacobson et al, Journal of Medicinal Chemistry (1993) 36, 1333.*

* cited by examiner

*Primary Examiner*—Mark L Berch

(57) ABSTRACT

The present invention provides processes for making pyridyl-linked-xanthines of formula VII, from 5,6-diamino-1H-pyrimidine-2,4-diones of formula II and acylating agents of formula VI.

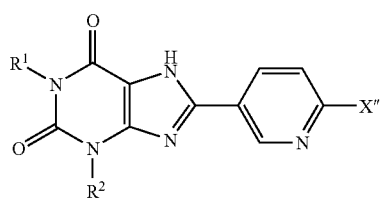

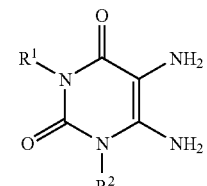

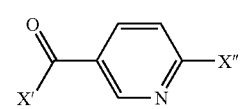

The xanthines are expected to be are selective antagonists of $A_{2B}$ adenosine receptors (ARs).

10 Claims, No Drawings

METHODS FOR THE SYNTHESIS OF UNSYMMETRICAL CYCLOALKYL SUBSTITUTED XANTHINES

This application claims priority to application Ser. No. 60/656,104, filed Feb. 25, 2005, the contents of which are hereby incorporated by reference in their entirety.

FIELD OF THE INVENTION

The present invention relates to methods for the synthesis of compounds and pharmaceutical compositions that are selective antagonists of $A_{2B}$ adenosine receptors (ARs). These compounds and compositions are useful as pharmaceutical agents.

BACKGROUND OF THE INVENTION

The alkylxanthine theophylline (compound A) a weak non-selective

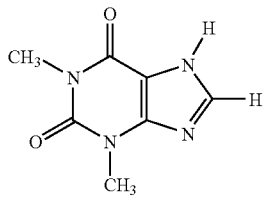

A adenosine antagonist (See Linden, J., et al., *Cardiovascular Biology of Purines*, eds. G. Burnstock, et al., 1998, pp 1-20) is useful therapeutically for the treatment of asthma. However, its use is associated with unpleasant side effects, such as insomnia and diuresis. In recent years, the use of theophylline as a bronchodilator for relief of asthma has been supplanted by drugs of other classes, i.e., selective $\beta_2$-adrenergic agonists, corticosteroids, and recently leukotriene antagonists. These compounds also have limitations and therefore the development of a theophylline-like drug with reduced side effects is still desirable.

It has been recognized that theophylline and its closely related analogue caffeine block endogenous adenosine acting as a local modulator of adenosine receptors in the brain and other organs at therapeutically useful doses. Adenosine activates four subtypes of G protein-coupled adenosine receptors (ARs), $A_1/A_{2A}/A_{2B}/A_3$. Enprofylline, (compound B), is another example of a xanthine

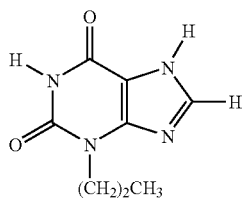

B that has been reported to block $A_{2B}$ adenosine receptors and is used to treat asthma. However, this compound only weakly blocks $A_1$, $A_{2A}$ and $A_3$ adenosine receptors. It has also been shown by LaNoue et al (U.S. Pat. No. 6,060,481) that selective adenosine $A_{2B}$ antagonists are useful for improving insulin sensitivity in a patient.

It has been reported that therapeutic concentrations of theophylline or enprofylline block human $A_{2B}$ receptors, and it has been proposed that antagonists selective for this subtype may have potential use as antiasthmatic agents. (See Feoktistov, I., et al., *Pharmacol. Rev.* 1997, 49, 381-402; and Robeva, A. S., et al., *Drug Dev. Res.* 1996, 39, 243-252). Enprofylline has a reported $K_i$ value of 7 μM and is somewhat selective in binding to human $A_{2B}$ ARs. (See Robeva, A. S., et al., *Drug Dev. Res.* 1996, 39, 243-252 and Linden, J., et al., *Mol. Pharmacol.* 1999, 56, 705-713). $A_{2B}$ ARs are expressed in some mast cells, such as the BR line of canine mastocytoma cells, which appear to be responsible for triggering acute $Ca^{2+}$ mobilization and degranulation. (See Auchampach, J. A., et al., *Mol. Pharmacol.* 1997, 52, 846-860 and Forsyth, P., et al., *Inflamm. Res.* 1999, 48, 301-307). $A_{2B}$ ARs also trigger $Ca^{2+}$ mobilization, and participate in a delayed IL8 release from human HMC-1 mast cells. Other functions associated with the $A_{2B}$ AR are the control of cell growth and gene expression, (See Neary, J., et al., *Trends Neurosci.* 1996, 19, 13-18) endothelial-dependent vasodilation (See Martin, P. L., et al., *J. Pharmacol. Exp. Ther.* 1993, 265, 248-253), and fluid secretion from intestinal epithelia. (See Strohmeier, G. R., et al., *J. Biol. Chem.* 1995, 270, 2387-2394). Adenosine acting through $A_{2B}$ ARs has also been reported to stimulate chloride permeability in cells expressing the cystic fibrosis transport regulator. (See Clancy, J. P., et al., *Am. J. Physiol.* 1999, 276, C361-C369.)

Recently Linden et al (U.S. Pat. No. 6,545,002) have described a new group of compounds and pharmaceutical compositions that are selective antagonists of $A_{2B}$ adenosine receptors (ARs).

Although adenosine receptor subtype-selective probes are available for the $A_1$, $A_{2A}$, and $A_3$ ARs, few selective antagonists and no selective agonists are known for the $A_{2B}$ receptor. Therefore, a continuing need exists for compounds that are selective $A_{2B}$ receptor antagonists.

SUMMARY OF THE INVENTION

The present invention provides a process for preparing a compound of the formula I:

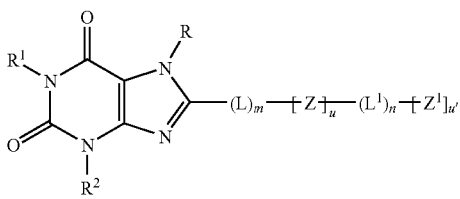

I wherein:
R is hydrogen or is selected from the group consisting of $(C_{1-5})$alkyl, halo$(C_{1-8})$alkyl, $(C_{3-8})$cycloalkyl, $(C_{3-8})$cycloalkyl$(C_{1-8})$alkyl-, $(C_{3-5})$alkenyl and $(C_{3-5})$alkynyl, unsubstituted;

$R^1$ is $(C_{3-8})$cycloalkyl;

$R^2$ is hydrogen, or is selected from the group consisting of substituted or unsubstituted $(C_{1-8})$alkyl, halo$(C_{1-8})$alkyl, $(C_{3-8})$alkenyl, $(C_{3-8})$alkenyl$(C_{1-8})$alkyl, $(C_{3-8})$alkynyl, $(C_{3-8})$alkynyl$(C_{1-8})$alkyl, $(C_{1-8})$alkoxy, $(C_{3-8})$cycloalkyl, $(C_{3-8})$cycloalkyl$(C_{1-8})$alkyl-, $(C_{4-10})$heterocyclyl, $(C_{4-10})$heterocyclyl$(C_{1-8})$alkyl-, $(C_{6-10})$aryl, $(C_{6-10})$aryloxy, $(C_{6-10})$aryl$(C_{1-8})$alkyl-, $(C_{5-10})$heteroaryl and $(C_{5-10})$heteroaryl$(C_{1-8})$alkyl-;

L and L¹ are each independently a substituted or unsubstituted linker comprising 1, 2, 3 or 4 linking atoms selected from the group consisting of carbon, nitrogen, oxygen, sulfur and phosphorus;

u and u' are each independently 0 or 1,

Z and Z¹ are each independently a 5-14 member substituted or unsubstituted monocyclic or polycyclic aryl or heteroaryl ring; and m is 0, 1 or 2; n is 0, 1 or 2; or a pharmaceutically acceptable salt thereof;

the process comprising:

a) contacting a 5,6-diamino-1H-pyrimidine-2,4-dione of formula II:

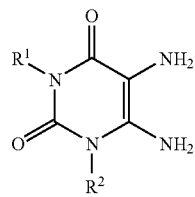

with an acylating agent of the formula III:

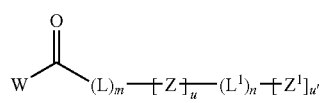

in an aprotic solvent to produce a 1H-pyrimidine-2,4-dione of formula IV: and

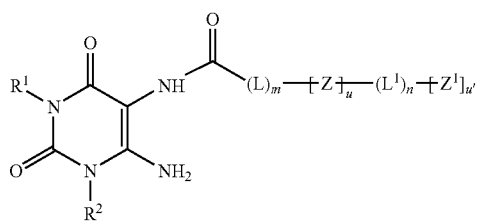

b) contacting the 1H-pyrimidine-2,4-dione of formula IV with a base to produce a xanthine of the formula V:

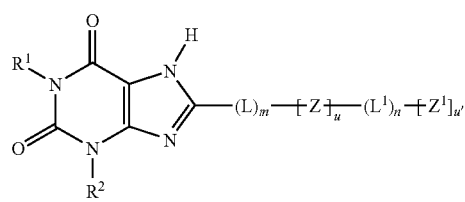

wherein W is a leaving group.

DETAILED OF THE INVENTION

The following definitions are used, unless otherwise described:

"Halo" means fluoro, chloro, bromo, or iodo.

"Alkyl", "alkoxy", "alkenyl", "alkynyl", etc. denote both straight and branched groups; but reference to an individual radical such as "propyl" embraces only the straight chain radical, a branched chain isomer such as "isopropyl" being specifically referred to. "$C_{X-Y}$alkyl" are used where X and Y indicate the number of carbon atoms in the chain. For example, $C_{1-4}$alkyl include alkyl groups that have a chain between 1 and 4 carbon atoms (e.g. methyl, ethyl, propyl, isopropyl, butyl, sec-butyl, isobutyl, etc.). When alkyl can be partially unsaturated, the alkyl chain may comprise one or more (e.g. 1, 2, 3, or 4) double or triple bonds in the chain.

"Amino" denotes a nitrogen moiety having two substituents attached to the nitrogen atom. Examples of an amino group include —NH₂, —NH₂NH₂, —NH₂NHCH₃, —NHCH₂CH₃, and the like. The two substituents attached to the nitrogen atom may be combined with the nitrogen to form a saturated or unsaturated ring. The amino group may be derivatized with other functional groups such as amino protecting groups that are well known in the art such as those described in *Protective Groups in Organic Synthesis*, T. W. Greene, John Wiley & Sons, New York, 1981 or the latest edition, and related texts.

"Aryl" denotes a phenyl radical or an ortho-fused bicyclic carbocyclic radical having about nine to ten ring atoms in which at least one ring is aromatic.

"Arylalkyl" or "($C_{6-10}$)aryl($C_{1-8}$)alkyl-" refer to a group of the formula aryl($C_{1-8}$)alkyl-, where aryl and ($C_{1-8}$)alkyl are as defined herein.

"Carbonyl" as used herein is the radical group "—CO—" and may include various carbonyl derivatives including carboxyls, carboxylate salts, carboxylate esters, thioesters, ketones, amides, carbamates and the like.

"Heterocycle" encompasses a cyclic radical attached or linked via a nitrogen or carbon ring atom of a monocyclic, fused-bicyclic, or bridged-bicyclic, saturated or unsaturated, ring system containing 5-10 ring atoms and preferably from 5-6 ring atoms, consisting of carbon and one, two, three or four heteroatoms including, for example, non-peroxide oxy (—O—), thio (—S—), sulfinyl (—SO—), sulfonyl (—S(O)₂—), amine —N(R)—, —N(O)—, —N=, phosphorus (—P—), —P(O)— and the like, wherein the group R is as defined herein, and optionally containing 1-3 double bonds (e.g., —CH═CH— or —CH═N—). Fully unsaturated heterocycles may also be defined as "heteroaryls." Heterocycle includes, for example, tetrahydrofuryl, dihydrofuryl, tetrahydroimidazolyl, azanorbornyl, pyrrolidyl, piperidyl, piperizyl, morpholinyl, azepinyl, 1,3-diazepinyl, 1,3-benzodiazepinyl, 1,4-diazepinyl, 1,4-benzodiazepinyl, 1,5-diazepinyl, 1,5-benzodiazepino and the like.

"Heteroaryl" encompasses a radical attached via a ring atom of a monocyclic or bicyclic aromatic ring containingt5-14 ring atoms, such as a monocyclic containing from 5-6 ring atoms, comprising carbon and one, two, three or four heteroatoms including, for example, non-peroxide oxy (—O—), thio (—S—), sulfinyl (—SO—), sulfonyl (—S(O)₂—), amine —N(R)—, —N(O)—, —N= and the like, wherein the group R is as defined herein. Bicyclic or tricyclic heteroaryls include, but are not limited to, those derived from benzo[b]furan, benzo[b]thiophene, benzimidazole, imidazo[4,5-c]pyridine, quinazoline, thieno[2,3-c]pyridine, thieno[3,2-b]pyridine, thieno[2,3-b]pyridine, indolizine, imidazo[1,2a]pyridine, quinoline, isoquinoline, phthalazine, quinoxaline, naphthyridine, quinolizine, indole, isoindole, indazole, indoline, benzoxazole, benzopyrazole, benzothiazole, imidazo[1,5-a]pyridine, pyrazolo[1,5-a]pyridine, pteridine, purine, carbazole, acridine and the like. Preferred heteroaryl groups include imidazolyl, triazolyl, triazinyl, oxazoyl, isoxazoyl, thiazolyl, isothiazoyl, thiodiazolyl, pyrrolyl, pyrazolyl, pyrazinyl, tetrazolyl, pyridinyl, pyrimidinyl, indolyl, isoquinolyl, quinolyl and the like.

"Isomers" as used herein means any compound having an identical molecular formulae but differing in the nature or sequence of bonding of their atoms or in the arrangement of their atoms in space. Isomers that differ in the arrangement of their atoms in space are termed "stereoisomers" that may be enantiomers or diastereomers. A carbon atom bonded to four nonidentical substituents is termed a "chiral center" and such compounds containing a chiral center may be termed a chiral compound. Conventions for stereochemical nomenclature, methods for the determination of stereochemistry and the separation of stereoisomers are well known in the art from standard texts such as "Advanced Organic Chemistry", 4th edition, March, Jerry, John Wiley & Sons, New York, 1992, and "Introduction to Organic Chemistry", latest edition, A. Streitwieser, Jr. & C. H. Heathcock, MacMillan Publishing Co., Inc. New York.

A "leaving group" as used herein, is a moiety that may be displaced in a chemical transformation, such as a nucleophilic displacement reaction, an acylation reaction and the like; and non-exclusive examples of such moiety include hydrogen, hydroxyl, halides, triflates, mesylate, tosylate, acetate, triazolyl, imidazolyl or cyano, and the like.

The present invention is intended to encompass all pharmaceutically acceptable ionized forms (e.g., salts) and solvates (e.g., hydrates) of the compounds, regardless of whether such forms and solvates are specified, as it is well known in the art that pharmaceutical agents in an ionized or solvated form may be used. Unless a particular stereochemistry is specified, recitation of a compound is intended to encompass all possible stereoisomers (e.g., enantiomers or diastereomers), independent of whether the compound is present as an individual isomer or a mixture of isomers. A recitation of a compound is intended to include all possible resonance forms and isomers. Claims to the compound of the present invention is intended to encompass the compound and all pharmaceutically acceptable ionized forms and solvates, all possible stereoisomers, resonance forms and isomers, unless otherwise specifically specified.

"Pharmaceutically acceptable salts" means salts of the compounds of the present invention which are pharmaceutically acceptable and which have the desired pharmacological activity. Such salts include acid addition salts formed with inorganic acids such as hydrochloric acid, hydrobromic acid, sulfuric acid, nitric acid, phosphoric acid, and the like. The salt may also be formed with organic acids including acetic acid, propionic acid, hexanoic acid, heptanoic acid, glycolic acid, pyruvic acid, lactic acid, malonic acid, succinic acid, malic acid, maleic acid, fumaric acid, tartatic acid, citric acid, benzoic acid, gluconic acid, glutamic acid, and the like.

Prodrugs of the compounds of the present invention may also be administered. As is known in the art, prodrugs are altered in vivo and become a compound of the present invention. All standard methods of using the compounds of the present invention are intended, whether prodrug delivery is specified, to encompass the administration of a prodrug that is converted in vivo to a compound according to the present invention. Also, some compounds of the present invention may be altered in vivo prior to being biologically active as selective antagonists of $A_{2B}$ adenosine receptors, and therefore, may themselves be prodrugs for another compound.

"Thio" as used as a substituent herein, means the group —S—, —SO—, —SO$_2$—, —SO$_3$— and their derivatives including, for example, —S-alkyl, —S-aryl, —S-heteroaryl, —SO-aryl, —SO-heteroaryl, —SO—NR'R", —SO$_2$NR'R" and the like, wherein the groups R' and R" are as defined herein.

As is recognized by one of ordinary skill in the art, the imidazole ring of the compounds of the present invention may exist in isomeric forms or as isomers, and thus are also included within the scope of the invention. For example, the isomers are represented as the structures (Ia) and (Ib):

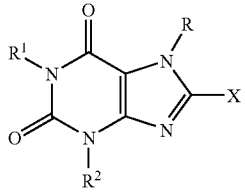

(Ia)

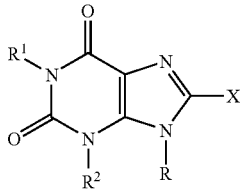

(Ib)

By naming or referring to one compound I, for example, it is understood for the purposes of the present application that the isomers (Ia) and (Ib) are also intended. Similarly, by referring to compound (Ia), it is understood for the purposes of the present application that the isomers I and (Ib) are also intended. The same holds true for references to isomer (Ib).

"Optional" or "optionally" mean that the subsequently described event or condition may but need not occur, and that the description includes instances where the event or condition occurs and instances in which it does not. For example, "optionally substituted" means that the named substituent may be present but need not be present, and the description includes situations where the named substituent is included and situations where the named substituent is not included.

The terms "include", "for example", "such as", and the like are used illustratively and are not intended to limit the present invention.

The indefinite articles "a" and "an" mean "at least one" or "one or more" when used in this application, including the claims, unless specifically indicated otherwise.

It will be appreciated by those skilled in the art that compounds of the invention having a chiral center may exist in and be isolated in optically active, and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase) and how to determine, for example, anti-tumor activity, herbicidal activity, or other therapeutic activity using the standard tests described herein, or using other similar tests which are well known in the art.

Specific and preferred values listed below for radicals, substituents, and ranges, are for illustration only; they do not exclude other defined values or other values within defined ranges for the radicals and substituents.

Specifically, $(C_{1-8})$alkyl can be methyl, ethyl, n-propyl, isopropyl, n-butyl, iso-butyl, sec-butyl, tert-butyl, n-pentyl, isopentyl, 3-pentyl, n-hexyl, n-heptyl, n-octyl or the branched $(C_{3-8})$alkyl; $(C_{2-8})$alkenyl can be vinyl, 1-propenyl, 2-propenyl (allyl), 1-butenyl, 2-butenyl, 3-butenyl, 1-pentenyl, 2-pentenyl, 3-pentenyl, 1-hexenyl, 2-hexenyl, 3-hexenyl, 1-heptenyl, 2-heptenyl, 3-heptenyl, 1-octenyl, 2-octenyl, 3-octenyl, 4-octenyl or the branched $(C_{3-8})$alkenyl; $(C_{3-8})$alkenyl can be 2-propenyl (allyl), 2-butenyl, 3-butenyl, 2-pentenyl, 3-pentenyl, 1-hexenyl, 2-hexenyl, 3-hexenyl, 2-heptenyl, 3-heptenyl, 2-octenyl, 3-octenyl, 4-octenyl, or the branched $(C_{3-8})$alkenyl; $(C_{2-8})$alkynyl can be ethynyl, 1-propynyl, 2-propynyl (propargyl), 1-butynyl, 2-butynyl, 3-butynyl, 1-pentynyl, 2-pentynyl, 3-pentynyl, 1-hexynyl, 2-hexynyl, 3-hexynyl, 1-heptynyl, 2-heptynyl, 3-heptynyl, 1-octynyl, 2-octynyl, 3-octynyl, 4-octynyl, or the branched $(C_{3-8})$alkynyl; $(C_{3-8})$alkynyl can be 2-propynyl (propargyl), 2-butynyl, 3-butynyl, 1-pentynyl, 2-pentynyl, 3-pentynyl, 1-hexynyl, 2-hexynyl, 3-hexynyl, 1-heptynyl, 2-heptynyl, 3-heptynyl, 1-octynyl, 2-octynyl, 3-octynyl, 4-octynyl, or the branched $(C_{3-8})$alkynyl; $(C_{1-8})$alkoxy can be methoxy, ethoxy, n-propoxy, isopropoxy, n-butoxy, iso-butoxy, sec-butoxy, tert-butoxy, pentoxy, 3-pentoxy, n-hexyloxy, n-heptyloxy, n-octyloxy, or the branched $(C_{3-8})$alkoxy; halo$(C_{1-8})$alkyl can be iodomethyl, bromomethyl, chloromethyl, fluoromethyl, trifluoromethyl, 2-chloroethyl, 2-bromoethyl, 2-fluoroethyl, 3-fluoropropyl, 2,2,2-trifluoroethyl, pentafluoroethyl, or the branched halo$(C_{3-8})$alkyl; $(C_{3-8})$cycloalkyl can be cyclopropyl, cyclobutyl, cyclopentyl, cyclohexyl, cycloheptyl or cyclooctyl; $(C_{3-8})$cycloalkyl$(C_{1-8})$alkyl- can be cyclopropylmethyl, cyclobutylmethyl, cyclopentylmethyl, cyclohexylmethyl, 2-cyclopropylethyl, 2-cyclobutylethyl, 2-cyclopentylethyl or 2-cyclohexylethyl; $(C_{6-10})$aryl can be phenyl, indenyl or naphthyl.

A "substituted" group, such as a substituted alkyl group or a substituted aryl group, means that one or more of the hydrogen atom on the alkyl or aryl group is replaced by the specified substituent or substituents as known in the art.

Arylalkyl can be, for example, phenylethyl, benzyl, 2-phenylpropyl, 3-phenylpropyl, 2-naphthylmethyl or 3-naphthylmethyl; and heteroaryl can be, for example, imidazolyl, triazolyl, triazinyl, oxazoyl, isoxazoyl, thiazolyl, isothiazoyl, pyrrolyl, pyrazinyl, tetrazolyl, pyridyl, pyrimidinyl, indolyl, isoquinolyl, quinolyl, or an oxide thereof.

The $(C_{1-8})$alkyl groups can be methyl, ethyl, propyl, butyl, pentyl, hexyl, heptyl, and octyl; alkenyl groups may include, for example, ethenyl, propenyl, butenyl, pentenyl and hexenyl.

Specific cycloalkyl groups are cyclopropyl, cyclobutyl, cyclopentyl and cyclohexyl.

Specific cycloalkylalkyl groups include, for example, cyclopropylmethyl, cyclobutylmethyl, cyclopropylethyl, cyclopentylmethyl, cyclohexylmethyl, 2-cyclopentylethyl, and 2-cyclohexylethyl.

Aspects of the Invention:

In one aspect of the invention, there is provided a process for preparing a compound of the formula I:

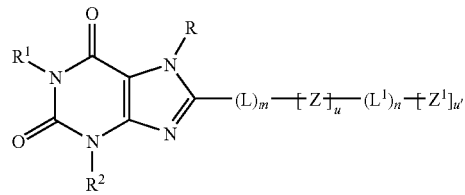

wherein: R is hydrogen or is selected from the group consisting of $(C_{1-5})$alkyl, halo$(C_{1-8})$alkyl, $(C_{3-8})$cycloalkyl, $(C_{3-8})$cycloalkyl$(C_{1-8})$alkyl-, $(C_{3-5})$alkenyl and $(C_{3-5})$alkynyl, each substituted or unsubstituted;

$R^1$ is $(C_{3-8})$cycloalkyl;

$R^2$ is hydrogen, or is selected from the group consisting of substituted or unsubstituted $(C_{1-8})$alkyl, halo$(C_{1-8})$alkyl, $(C_{3-8})$alkenyl, $(C_{3-8})$alkenyl$(C_{1-8})$alkyl, $(C_{3-8})$alkynyl, $(C_{3-8})$alkynyl$(C_{1-8})$alkyl, $(C_{1-8})$alkoxy, $(C_{3-8})$cycloalkyl, $(C_{3-8})$cycloalkyl$(C_{1-8})$alkyl-, $(C_{4-10})$heterocyclyl, $(C_{4-10})$heterocyclyl$(C_{1-8})$alkyl-, $(C_{6-10})$aryl, $(C_{6-10})$aryloxy, $(C_{6-10})$aryl$(C_{1-8})$alkyl-, $(C_{5-10})$heteroaryl and $(C_{5-10})$heteroaryl$(C_{1-8})$alkyl-;

L and $L^1$ are each independently a substituted or unsubstituted linker comprising 1, 2, 3 or 4 linking atoms selected from the group consisting of carbon, nitrogen, oxygen, sulfur and phosphorus;

u and u' are each independently 0 or 1,

Z and $Z^1$ are each independently a 5-14 member substituted or unsubstituted monocyclic or polycyclic aryl or heteroaryl ring; and m is 0, 1 or 2; n is 0, 1 or 2; or a pharmaceutically acceptable salt thereof;

the process comprising: a) contacting a 5,6-diamino-1H-pyrimidine-2,4-dione of formula II:

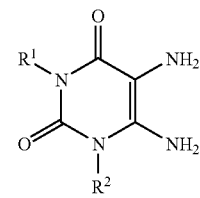

with an acylating agent of the formula III:

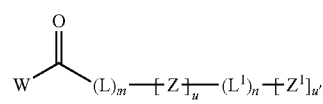

in an aprotic solvent to produce a 1H-pyrimidine-2,4-dione of formula IV: and

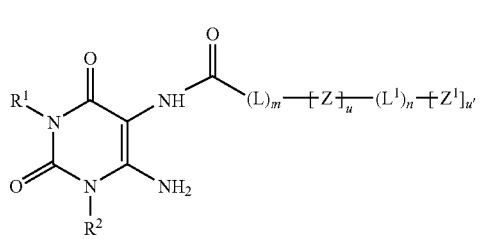

IV b) contacting the 1H-pyrimidine-2,4-dione of formula IV with a base to produce a xanthine of the formula V:

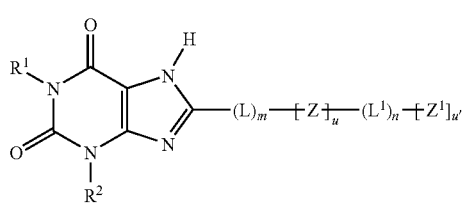

V wherein W is a leaving group. In one variation of the process, the aprotic solvent is an amine. In another variation, the aprotic solvent is a mixture of DICHLOROMETHANE and pyridine. In another variation of the process, the base is a metal hydroxide selected from the group consisting of lithium hydroxide, calcium hydroxide, sodium hydroxide, potassium hydroxide, and mixtures thereof. In a particular variation of the process, the base is sodium hydroxide.

In another aspect, there is provided the above process, wherein the 1H-pyrimidine-2,4-dione of formula IV is prepared and is converted to the xanthine of the formula V without further purification. In one variation of the process, Z is a substituted or unsubstituted monocyclic or polycyclic heteroaryl ring comprising at least one nitrogen ring atom. In another variation, Z is a substituted or unsubstituted heteroaryl ring selected from the group consisting of benzo[b]furan, benzo[b]thiophene, benzimidazole, imidazo[4,5-c]pyridine, quinazoline, thieno[2,3-c]pyridine, thieno[3,2-b]pyridine, thieno[2,3-b]pyridine, indolizine, imidazo[1,2a]pyridine, quinoline, isoquinoline, phthalazine, quinoxaline, naphthyridine, quinolizine, indole, isoindole, indazole, indoline, benzoxazole, benzopyrazole, benzothiazole, imidazo[1,5-a]pyridine, pyrazolo[1,5-a]pyridine, pteridine, purine, carbazole, acridine, imidazolyl, triazolyl, triazinyl, oxazoyl, isoxazoyl, thiazolyl, isothiazoyl, thiodiazolyl, pyrrolyl, pyrazolyl, pyrazinyl, tetrazolyl, pyridinyl, pyrimidinyl, indolyl, isoquinolyl and quinolyl.

In another aspect, there is provided the above process wherein the acylating agent is a compound of the formula VI:

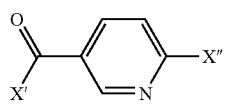

VI wherein X' and X" are each independently Cl, Br or I, and the xanthine that is formed is a compound of the formula VII:

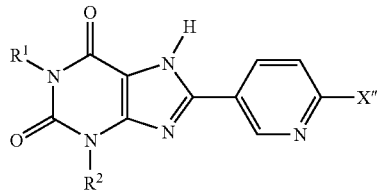

VII wherein:

R$^1$ is (C$_{3-8}$)cycloalkyl; and

R$^2$ is hydrogen, or is selected from the group consisting of substituted or unsubstituted (C$_{1-8}$)alkyl, halo(C$_{1-8}$)alkyl, (C$_{3-8}$)alkenyl, (C$_{3-8}$)alkenyl(C$_{1-8}$)alkyl, (C$_{3-8}$)alkynyl, (C$_{3-8}$)alkynyl(C$_{1-8}$)alkyl, (C$_{1-8}$)alkoxy, (C$_{3-8}$)cycloalkyl, (C$_{3-8}$)cycloalkyl(C$_{1-8}$)alkyl-, (C$_{4-10}$)heterocyclyl, (C$_{4-10}$)heterocyclyl(C$_{1-8}$)alkyl-, (C$_{6-10}$)aryl, (C$_{6-10}$)aryloxy, (C$_{6-10}$)aryl(C$_{1-8}$)alkyl-, (C$_{5-10}$)heteroaryl and (C$_{5-10}$)heteroaryl(C$_{1-8}$)alkyl-.

In one variation of the above process, the acylating agent is a compound selected from the group consisting of:

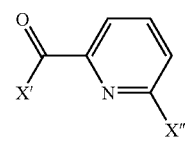

VIa

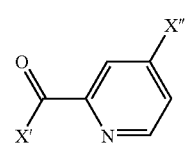

VIb

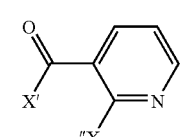

VIc

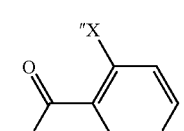

VId

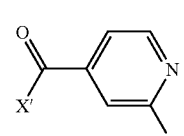

VIe wherein the xanthine products formed (VIIa-VIIe) are the products that correspond to the acylating agent employed above. In another variation of the above process, the compound of the formulae VII and VIIa-VIIe are further contacted with an amine of the formula R'—NH$_2$ to produce a compound of the formula VIII and the isomers of formulae VIIIa-VIIIe;

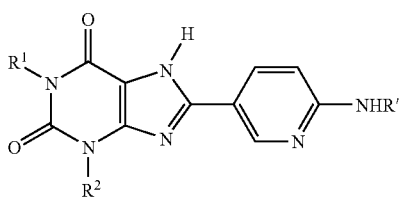

VIII which is further contacted with a compound of the formula Z$^1$C(O)—W to form a compound of the formula IX and the isomers of formulae IXa-IXe:

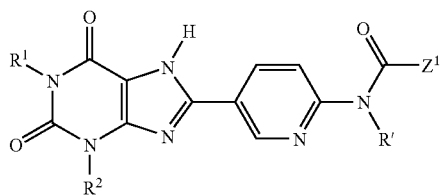

IX wherein:
R' is selected from the group consisting of amino, (C$_{1-4}$) alkyl, halo(C$_{1-4}$)alkyl, (C$_{3-8}$)alkenyl, (C$_{3-8}$)alkynyl, (C$_{1-4}$)alkoxy(C$_{1-4}$)alkyl, R$^4$R$^5$N(C$_{1-4}$)alkyl, R$^4$R$^5$NC(O)(C$_{1-4}$)alkyl-, (C$_{3-6}$)cycloalkyl, (C$_{3-6}$)cycloalkyl(C$_{1-4}$)alkyl-, (C$_{4-10}$)heterocyclyl(C$_{1-4}$)alkyl-, (C$_{6-10}$)aryl(C$_{1-4}$)alkyl-, and (C$_{5-10}$)heteroaryl(C$_{1-8}$)alkyl-, each substituted or unsubstituted;

R' is (C$_{3-8}$)cycloalkyl; and

R$^2$ is hydrogen, or is selected from the group consisting of substituted or unsubstituted (C$_{1-8}$)alkyl, halo(C$_{1-8}$)alkyl, (C$_{3-8}$)alkenyl, (C$_{3-8}$)alkenyl(C$_{1-8}$)alkyl, (C$_{3-8}$)alkynyl, (C$_{3-8}$)alkynyl(C$_{1-8}$)alkyl, (C$_{1-8}$)alkoxy, (C$_{3-8}$)cycloalkyl, (C$_{3-8}$)cycloalkyl(C$_{1-8}$)alkyl-, (C$_{4-10}$)heterocyclyl, (C$_{4-10}$)heterocyclyl(C$_{1-8}$)alkyl-, (C$_{6-10}$)aryl, (C$_{6-10}$)aryloxy, (C$_{6-10}$)aryl(C$_{1-8}$)alkyl-, (C$_{5-10}$)heteroaryl and (C$_{5-10}$)heteroaryl(C$_{1-8}$)alkyl-;

Z$^1$ is a 5-14 member substituted or unsubstituted monocyclic or polycyclic aryl or heteroaryl ring; and R$^4$ and R$^5$ each are independently hydrogen or are selected from the group consisting of (C$_{1-8}$)alkyl, (C$_{3-8}$)alkenyl, (C$_{3-8}$)alkynyl, (C$_{1-8}$)alkoxy, (C$_{3-8}$)cycloalkyl, (C$_{3-8}$)cycloalkyl(C$_{1-8}$)alkyl-, (C$_{6-18}$)polycycloalkyl, (C$_{6-18}$)polycycloalkyl(C$_{1-8}$)alkyl-, (C$_{3-10}$)heterocyclyl, (C$_{3-10}$)heterocyclyl(C$_{1-8}$)alkyl-, ((C$_{1-8}$)alkyl)$_2$N—(C$_{6-10}$)aryl, (C$_{6-10}$)aryl(C$_{1-8}$)alkyl-, (C$_{5-10}$)heteroaryl(C$_{1-8}$)alkyl-, (C$_{1-8}$)C(O)—, (C$_{1-8}$)alkylCO$_2$—, —C(O)N((C$_{1-8}$)alkyl)$_2$, —S(O)(C$_{1-8}$)alkyl, —S(O)N((C$_{1-8}$)alkyl)$_2$, —S(O)$_2$(C$_{1-8}$)alkyl and —S(O)$_2$N((C$_{1-8}$)alkyl)$_2$.

In yet another variation of the above, the compound of the formula VII or the isomers of formulae VIIa-VIIe is further contacted with an amine of the formula R'—NHC(O)Z$^1$ at elevated temperatures to produce a compound of the formula VIIIa':

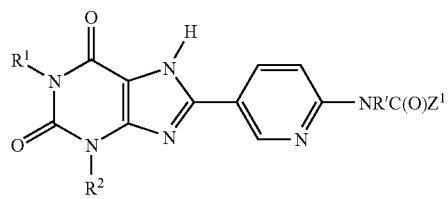

VIIIa' and the pyridinyl isomers of the formulae VIIIa to VIIIe; wherein: R' is selected from the group consisting of amino, (C$_{1-4}$)alkyl, halo(C$_{1-4}$)alkyl, (C$_{3-8}$)alkenyl, (C$_{3-8}$)alkynyl, (C$_{1-4}$)alkoxy(C$_{1-4}$)alkyl, R$^4$R$^5$N(C$_{1-4}$)alkyl-, R$^4$R$^5$NC(O)(C$_{1-4}$)alkyl-, (C$_{3-6}$)cycloalkyl, (C$_{3-6}$)cycloalkyl(C$_{1-4}$)alkyl-, (C$_{4-10}$)heterocyclyl(C$_{1-4}$)alkyl-, (C$_{6-10}$)aryl(C$_{1-4}$)alkyl- and (C$_{5-10}$)heteroaryl(C$_{1-8}$)alkyl-, each substituted or unsubstituted;

Z$^1$ is a 5-14 member substituted or unsubstituted monocyclic or polycyclic aryl or heteroaryl ring; and wherein R$^4$ and R$^5$ each are independently hydrogen or are selected from the group consisting of (C$_{1-8}$)alkyl, (C$_{3-8}$)alkenyl, (C$_{3-8}$)alkynyl, (C$_{1-8}$)alkoxy, (C$_{3-8}$)cycloalkyl, (C$_{3-8}$)cycloalkyl(C$_{1-8}$)alkyl-, (C$_{6-18}$)polycycloalkyl, (C$_{6-18}$)polycycloalkyl(C$_{1-8}$)alkyl-, (C$_{3-10}$)heterocyclyl, (C$_{3-10}$)heterocyclyl(C$_{1-8}$)alkyl-, ((C$_{1-8}$)alkyl)$_2$N—(C$_{6-10}$)aryl, (C$_{6-10}$)aryl(C$_{1-8}$)alkyl-, (C$_{5-10}$)heteroaryl, (C$_{5-10}$)heteroaryl(C$_{1-8}$)alkyl-, (C$_{1-8}$)alkyl)C(O)—, (C$_{1-8}$)alkyl CO$_2$—, —C(O)N((C$_{1-8}$)alkyl)$_2$, —S(O)(C$_{1-8}$)alkyl, —S(O)N((C$_{1-8}$)alkyl)$_2$, —S(O)$_2$(C$_{1-8}$)alkyl and —S(O)$_2$N((C$_{1-8}$)alkyl)$_2$. In one variation, the elevated temperature is about 75 to 185° C.

In another aspect, there is provided a process for preparing a compound of the formula II:

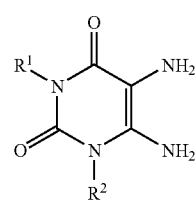

II wherein:
R$^1$ is (C$_{3-8}$)cycloalkyl; and R$^2$ is hydrogen, or is selected from the group consisting of substituted or unsubstituted (C$_{1-8}$)alkyl, halo(C$_{1-8}$)alkyl, (C$_{3-8}$)alkenyl, (C$_{3-8}$)alkenyl(C$_{1-8}$)alkyl, (C$_{3-8}$)alkynyl, (C$_{3-8}$)alkynyl(C$_{1-8}$) alkyl, (C$_{1-8}$)alkoxy, (C$_{3-8}$)cycloalkyl, (C$_{3-8}$)cycloalkyl (C$_{1-8}$)alkyl-, (C$_{4-10}$)heterocyclyl, (C$_{4-10}$)heterocyclyl (C$_{1-8}$)alkyl-, (C$_{6-10}$)aryl, (C$_{6-10}$)aryloxy, (C$_{6-10}$)aryl (C$_{1-8}$)alkyl-, (C$_{5-10}$)heteroaryl and (C$_{5-10}$)heteroaryl (C$_{1-8}$)alkyl-; the process comprising: a) contacting a compound of the formula X

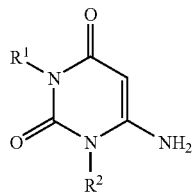

X with a nitration agent sufficient to form a compound of the formula XI, and

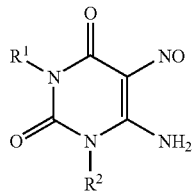

XI b) contacting the compound of the formula XI with a reducing agent for a time sufficient to form a compound of formula II. In one particular variation of the above process, the nitration agent is selected from the group consisting of $NaNO_2/AcOH$, $HNO_3/H_2SO_4$, $N_2O_5/P_2O_5/CCl_4$, HONO, $EtONO_2$, $CH_3COONO_2$ and $NO_2^+ CF_3SO_3^-$. In another particular variation, the nitration agent is $NaNO_2/AcOH$. In another variation of the process, the reducing agent is hydrogen and palladium on carbon or sodium dithionite.

In another aspect, there is provided a process for preparing a compound of the formula X:

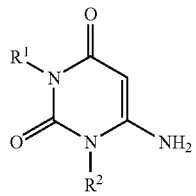

X $R^1$ is $(C_{3-8})$cycloalkyl; and $R^2$ is hydrogen, or is selected from the group consisting of substituted or unsubstituted $(C_{1-8})$alkyl, halo$(C_{1-8})$alkyl, $(C_{3-8})$alkenyl, $(C_{3-8})$alkenyl$(C_{1-8})$alkyl, $(C_{3-8})$alkynyl, $(C_{3-8})$alkynyl$(C_{1-8})$alkyl, $(C_{1-8})$alkoxy, $(C_{3-8})$cycloalkyl, $(C_{3-8})$cycloalkyl$(C_{1-8})$alkyl-, $(C_{4-10})$heterocyclyl, $(C_{4-10})$heterocyclyl$(C_{1-8})$alkyl-, $(C_{6-10})$aryl, $(C_{6-10})$aryloxy, $(C_{6-10})$aryl$(C_{1-8})$alkyl-, $(C_{5-10})$heteroaryl and $(C_{5-10})$heteroaryl$(C_{1-8})$alkyl-; comprising:

a) contacting a compound of the formula XII:

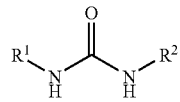

XII with a compound of the formula NC—$CH_2$—COOH with a dehydrating agent;

b) hydrolyzing the resulting reaction mixture to form a mixture of the compound of the formulae Xa and Xb; and

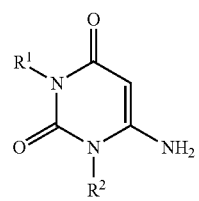

Xa

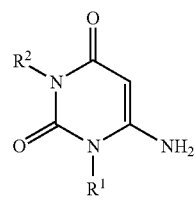

Xb c) separating the compound of the formula Xa from the formula Xb. In one variation of the above process, the dehydrating agent is selected from the group consisting of acetic anhydride, propionic anhydride and benzoic anhydride. In a particular variation, the dehydrating agent is acetic anhydride and the reaction is performed at about 80° C. In another variation of the process, the hydrolysis is performed with an aqueous alkaline salt in an alcoholic solvent. In yet another variation, the aqueous alkaline salt in an alcoholic solvent is aqueous NaOH and methanol. In another variation, the separation of Xa and Xb to obtain substantially pure X is performed by crystallization, chromatography or by derivatizing the compound mixtures into a separable derivatives, isolating the isomers and converting the isolated derivative back to the substantially pure isomer Xa or Xb. Methods for derivatizing or further reacting the compound mixture to form a derivative product mixture with the isomers having distinct physical characteristics such that the isomers may be separated are well known in the art of synthetic organic chemistry.

According to each of the above processes, there is provided the compound wherein $R^1$ is selected from the group consisting of cyclopropyl or cyclobutyl, and $R^2$ is selected from the group consisting of substituted or unsubstituted $(C_{1-8})$alkyl, halo$(C_{1-8})$alkyl, $(C_{3-8})$alkenyl, $(C_{3-8})$alkenyl$(C_{1-8})$alkyl, $(C_{3-8})$alkynyl, $(C_{3-8})$alkynyl$(C_{1-8})$alkoxy, $(C_{3-8})$cycloalkyl, $(C_{3-8})$cycloalkyl$(C_{1-8})$alkyl-, $(C_{4-10})$heterocyclyl, $(C_{4-10})$heterocyclyl$(C_{1-8})$alkyl, $(C_{6-10})$aryl, $(C_{6-10})$aryloxy, $(C_{6-10})$aryl$(C_{1-8})$alkyl-, $(C_{5-10})$heteroaryl and $(C_{5-10})$heteroaryl$(C_{1-8})$alkyl-. In one variation of the above, $R^1$ is selected from the group consisting of cyclopropyl and cyclobutyl, and $R^2$ is selected from the group consisting of substituted or unsubstituted $(C_{1-8})$alkyl, halo$(C_{1-8})$alkyl, $(C_{3-8})$alkenyl, $(C_{3-8})$alkenyl$(C_{1-8})$alkyl, $(C_{3-8})$alkynyl and $(C_{3-8})$alkynyl$(C_{1-8})$alkyl. In another variation, $R^1$ is cyclopropyl or cyclobutyl, and $R^2$ is a unsubstituted or substituted $(C_{1-8})$alkyl.

In one aspect, there is provided a compound comprising any one of the formulae:

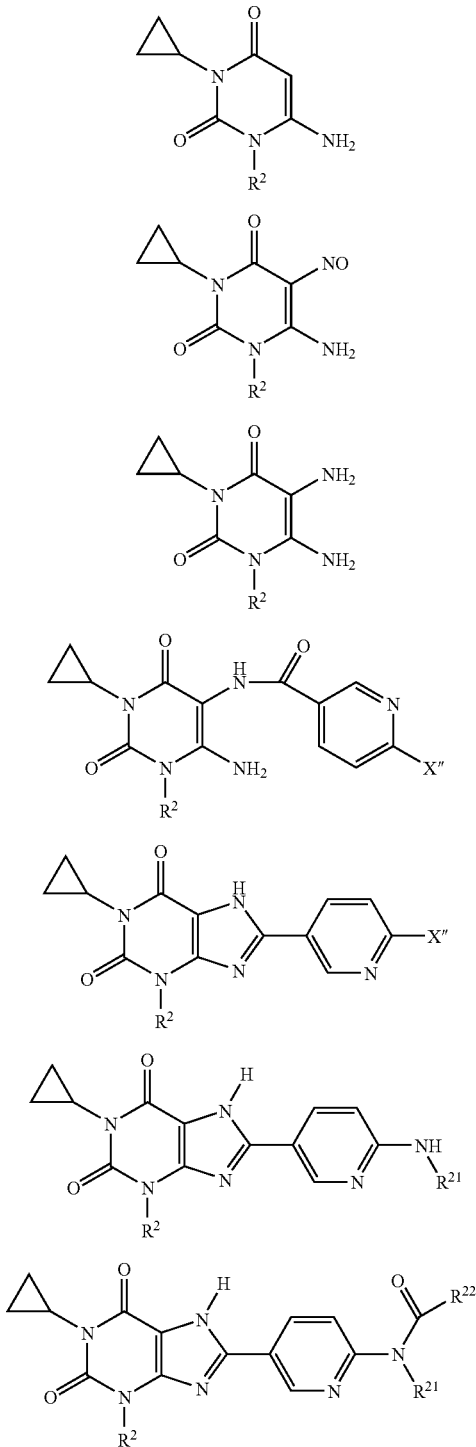

wherein $R^2$ is hydrogen, or is selected from the group consisting of substituted or unsubstituted $(C_{1-8})$alkyl, halo$(C_{1-8})$alkyl, $(C_{3-8})$alkenyl, $(C_{3-8})$alkenyl$(C_{1-8})$alkyl, $(C_{3-8})$alkynyl, $(C_{3-8})$alkynyl$(C_{1-8})$alkyl, $(C_{1-8})$alkoxy, $(C_{3-8})$cycloalkyl, $(C_{3-8})$cycloalkyl$(C_{1-8})$alkyl-, $(C_{4-10})$heterocyclyl, $(C_{4-10})$heterocyclyl$(C_{1-8})$alkyl-, $(C_{6-10})$aryl, $(C_{6-10})$aryloxy, $(C_{6-10})$aryl$(C_{1-8})$alkyl-, $(C_{5-10})$heteroaryl and $(C_{5-10})$heteroaryl$(C_{1-8})$alkyl-; $R^{21}$ and $R^{22}$ are each independently selected from the group consisting of hydrogen, or substituted or unsubstituted perhalo$(C_{1-8})$alkyl, amino, $(C_{1-8})$alkyl, $(C_{2-8})$alkene, $(C_{2-8})$alkyne, $(C_{3-12})$cycloalkyl, heterocycloalkyl, aryl$(C_{1-8})$alkyl, heteroaryl, $(C_{9-12})$bicycloaryl, hetero$(C_{8-12})$bicycloaryl, carbonyl group, thiocarbonyl, aryl, heteroaryl, $(C_{1-8})$alkoxy, aryloxy, heteroaryloxy; and X" is Br, Cl or I; or their pharmaceutically acceptable salt thereof.

Reaction Scheme 1 illustrates a general synthetic scheme for the preparation of compound I. Reaction Scheme 2 illustrates a representative procedure for the preparation of the compound of the present invention, as represented by the preparation of the xanthine derivative 9. Reaction Scheme 3 illustrates a representative procedure for the preparation of the compound of the present invention, as represented by the preparation of the xanthine derivatives 13, 14 and 15.

In Reaction Scheme 2, a bis-substituted urea, such as the asymmetrically substituted urea 1, may be prepared by the condensation of an amine with an isocyanate. Where such asymmetrically substituted urea such as compound 1 is desired, for example, the condensation of 1-cyclopropylamine with N-propyl-isocyanate affords the urea 1. The nature of the substitution on the urea nitrogen atoms, which ultimately corresponds to the N-1 and N-3 substituents of the xanthine derivative such as compound 9, will be determined by the nature of the amine and isocyanate employed in the condensation reaction. The condensation reaction may be performed in a polar or non-polar aprotic solvent at about −25° C. to about 50° C., depending the reactivities of the amine and the isocyanate reactants. Preferably, the reaction is performed in a hydrocarbon solvent such as toluene, and at a reaction temperature of about 0° C. to about 25° C. until the reaction is deemed complete. The product may be isolated by filtration and isolated in the usual way. Where further purification is desired, the product may be purified by crystallization or by chromatography, such as column chromatography.

The aminouracil derivative such as compound 2, may be prepared by contacting a substituted urea, such as compound 1 with 2-cyanoacetic acid with a dehydrating agent, such as an acid anhydride. For example, the di-alkyl urea compound 1 may be treated with an excess of cyanoacetic acid in acetic anhydride, and the resulting mixture may be heated above room temperature until the reaction is deemed complete. While a solvent may be added, typically, the reaction is performed without any additional solvent, and the reaction may be heated at about 50° C. to about 115° C., preferably at about 65° C. to about 100° C., more preferably at about 80° C. until the reaction is deemed complete. The acid anhydride may be removed from the reaction mixture by any methods, such as rotoevaporation or distillation under reduced pressure. The resulting residue may be dissolved in an aqueous alcoholic solvent such as methanol and 20% NaOH below room temperature, or about 0° C. to about 5° C. The resulting mixture may be stirred at the same temperature for about 1 hour and then warmed to about room temperature for about one hour. Excess solvent may be removed under reduced pressure and the resulting crude product may be isolated and purified.

In the case of the reaction of the dialkyl urea 1 with cyanoacetic acid, the resulting product is a mixture of the aminouracil 2 and 3, and substantially pure aminouracil 2 may be obtained by silica gel column chromatography or by HPLC with a C-18 column.

The 5-nitrosouracil derivatives such as compound of the formula 4 may be obtained by the nitrosylation of the aminouracil 2 using standard nitration reagents. Examples of such agents include, for example, $NaNO_2/AcOH$, $HNO_3/H_2SO_4$, $N_2O_5/P_2O_5/CCl_4$, HONO, $EtONO_2$, $CH_3COONO_2$ and $NO_2^+CF_3SO_3^-$ that forms the nitro or the nitrosouracil derivative. Thus, the aminouracil 2 may be dissolved in an aqueous acid, such as acetic acid and water below room temperature, such as about 10° C., and $NaNO_2$ in water is added to the aminouracil. When the reaction is deemed complete, the volatiles are removed under reduced pressure and the residue is redissolved in a mixture of solvents. Example of such mixtures of solvents include alcohols in an organic solvent, such as absolute ethanol in DICHLOROMETHANE. The resulting mixture is heated and the hot mixture may be filtered through a filter aid such as Celite 545 to remove insoluble inorganic salts. The solvent or solvent mixtures may evaporated under reduced pressure to afford the desired 5-nitrouracil or 5-nitrosouracil such as compound 4.

Reduction of the 5-nitrosouracil may be performed using various reagents known in the art for the reduction to nitro or nitroso compounds to the corresponding amine. Thus, the 5-nitrosouracil 4 may be dissolved in an alcoholic solvent such as absolute ethanol, and reduced using hydrogen gas and a catalyst, such as 10% Pd/C. Once the reaction is deemed complete, the resulting mixture may be filtered through a layer of Celite 545, and the volatiles removed under reduced pressure. The resulting product, '5,6-diaminouracil 5 may be further purified, or may used as is in the following reaction without further purification.

Acylation of the '5,6-diaminouracil 5 may be performed using various acylating agents as known in the art, and the reaction may be conducted in an aprotic solvent. Example of such aprotic solvent may be an amine, such as pyridine that may be used to form the acid salt of the amine. Thus, the '5,6-diaminouracil 5 may be treated with an acid halide, such as 6-chloronicotinoyl chloride in DICHLOROMETHANE and pyridine at about below room temperature, such as at about 5° C. and then warmed to about room temperature to drive the reaction to completion. Once the reaction is complete, the solvent is removed under reduced pressure to afford an oily residue. An aqueous base solution, such as 2N NaOH is added to the oil, and the resulting mixture is heated under reflux until the reaction is complete and the xanthine derivative is formed. The mixture is then cooled to about room temperature, and the pH is adjust to neutral pH, or about pH of 7 with acid, such as concentrated HCl. Once a solid product is formed, the product is collected by filtration and washed with water and organic solvent or solvent mixture, such as with diethyl ether and chloroform. The product, such as the 1-cyclopropyl-3-propyl-8-(6-chloro-3-pyridyl)xanthine 7 may used as is in the subsequent reaction without further purification, or if desired, the product may be further purified.

The xanthine, such as xanthine 7, may be further converted to the corresponding substituted amine by the reaction of the xanthine 7 with an amine under pressure, such as a sealed tube in a solvent, such as ethanol. The resulting mixture may be degassed and sealed under an inert atmosphere such as argon. The sealed reaction mixture may be heated at an elevated temperature, such as at about 100° C. to about 200° C. or at about 160° C. for about 48 to 60 hours, or until the reaction is deemed complete. After the mixture is cooled to room temperature and a solvent such as ether is added, and the solids are filtered to obtain the desired product such as compound 8.

Where the acylation of the compound of the formula 8 is desired to form the compound of the formula 2, acylation may be performed by contacting the amine of the formula 8 with an acyl halide such as an acyl chloride in a solvent and base, such as an amine base such as pyridine. The resulting mixture may be stirred at about room temperature for about 24 to about 60 hours until the reaction is deemed complete. Removal of the solvent under reduced pressure followed by purification, where desired, by column chromatography or crystallization, provides the desired acylated product such as the compound of the formula 9.

In each of the above processing step, where the resulting product from the reaction is the desired product or product mixtures, optionally, the intermediate compound(s) may be used in the subsequent step without further purification. However, as noted above, the purification and isolation of compound of formula 2 from the compound of formula 3, for example, is necessary at this particular step because the two isomers 2 and 3 cannot be readily separated in any subsequent steps. Thus, the isolation of the compound of formula 2 from the compound of formula 3 allows the preparation of the desired isomer in the subsequent processing steps.

REACTION SCHEME 1

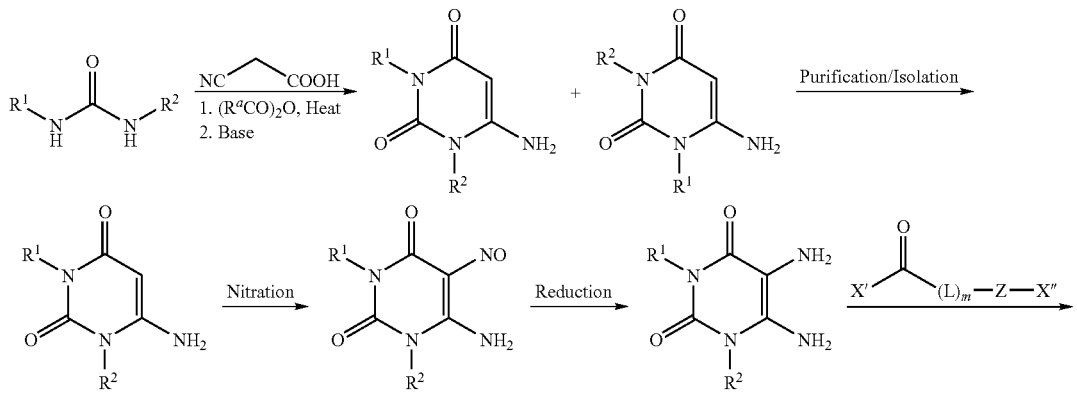

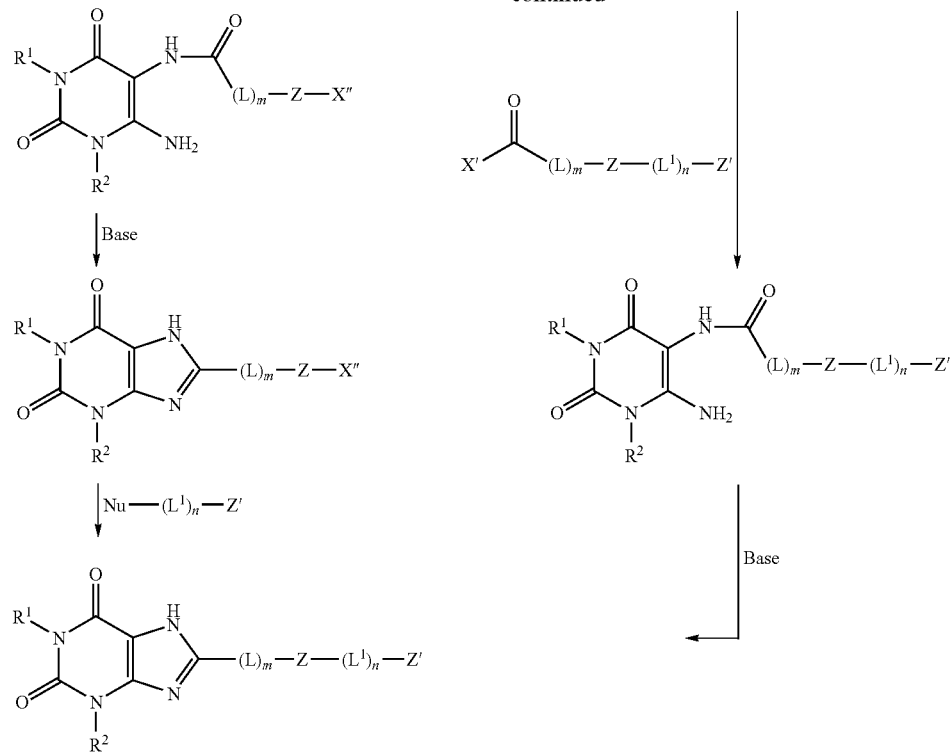
REACTION SCHEME 2
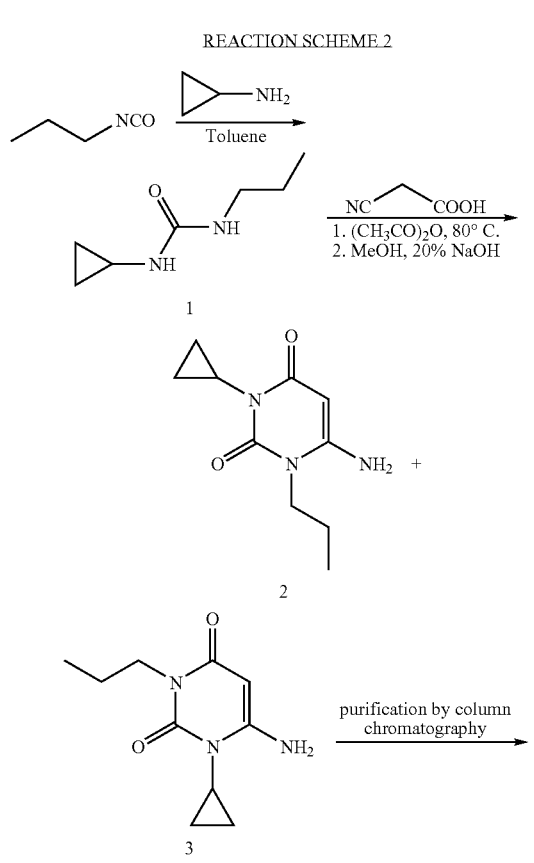
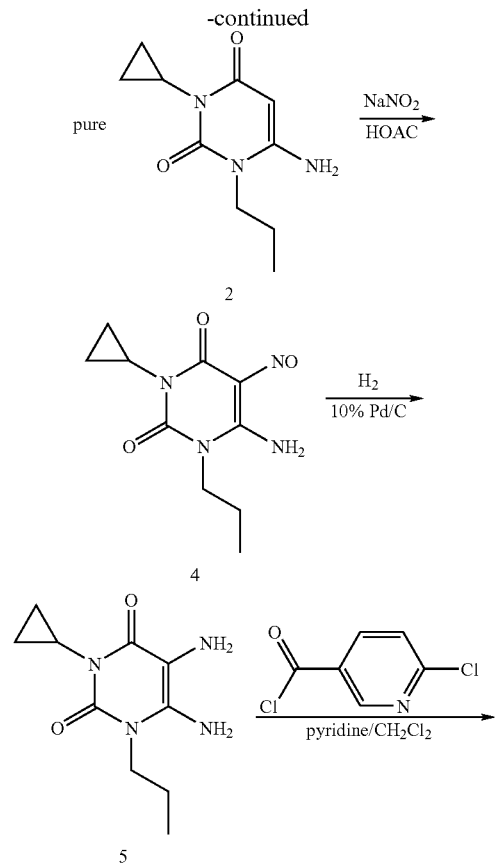

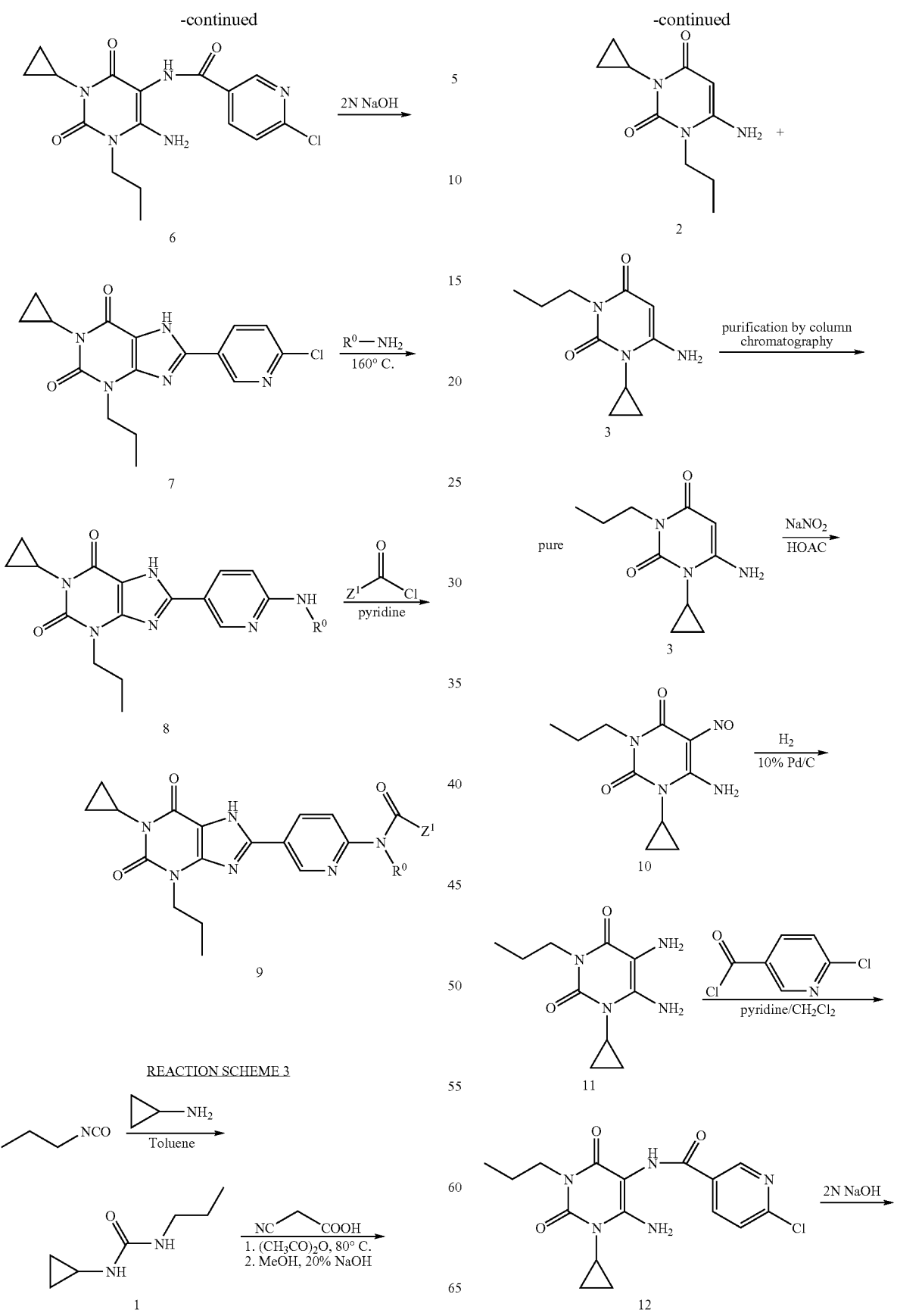

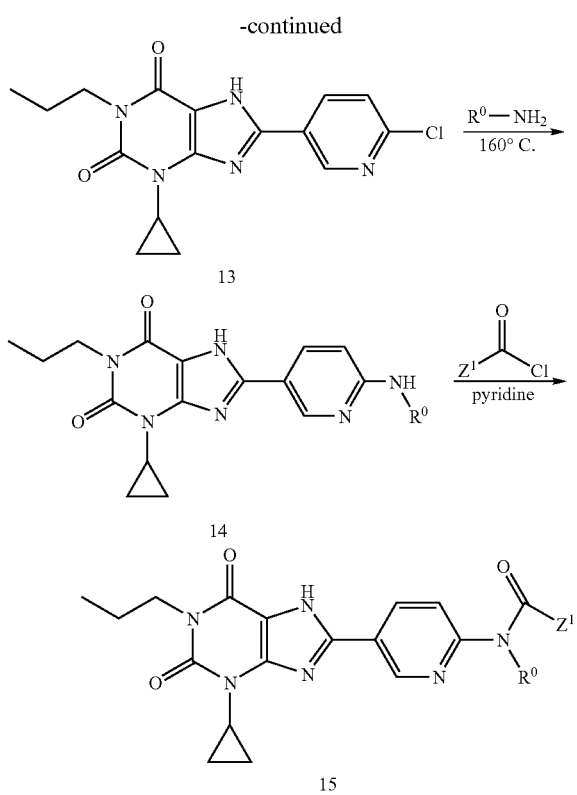

The following abbreviations have been used herein:
[$^{125}$I]ABA [$^{125}$I]N$^6$-(4-aminobenzyl)-adenosine
$^{125}$I-ABOPX $^{125}$I-3-(4-amino-3-iodobenzyl)-8-oxyacetate-1-propyl-xanthine
AR adenosine receptor
CGS 21680 2-[4-[(2-carboxyethyl)phenyl]ethyl-amino]-5□-N-ethylcarbamoyl adenosine
CPX 8-cyclopentyl-1,3-dipropylxanthine
DCM Dichloromethane
DMEM Dulbecco modified eagle medium
DMF N,N-dimethylformamide
DMSO dimethylsulfoxide
EDTA ethylenediaminetetraacetate
HEK cells human embryonic kidney cells
$K_i$ equilibrium inhibition constant
NECA 5'-(N-ethylcarbamoyl)adenosine
R-PIA R-N6-phenylisopropyladenosine
TEA triethylamine
TLC Thin layer chromatography
ZM 241385 4-(2-[7-amino-2-{furyl}{1,2,4}triazolo{2,3-a}{1,3,5}triazin-5-ylaminoethyl)phenol In cases where compounds are sufficiently basic or acidic to form stable nontoxic acid or base salts, administration of the compounds as salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic or stereoisomeric form or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis or by chromatographic separation using a chiral stationary phase). It is also conventional to determine $A_{2B}$ adenosine antagonist activity using the standard tests described herein or using other similar tests which are well known in the art.

The compounds of formula I can be formulated as pharmaceutical compositions and administered to a mammalian host, such as a human patient in a variety of forms adapted to the chosen route of administration, i.e., orally or parenterally, by intravenous, intramuscular, topical, inhalation or subcutaneous routes. Exemplary pharmaceutical compositions are disclosed in "Remington: The Science and Practice of Pharmacy", A. Gennaro, ed., 20th edition, Lippincott, Williams & Wilkins, Philadelphia, Pa.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula I to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508). Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the compound(s) of formula I in a liquid composition, such as a lotion, will be from about 0.1-25 wt-%, preferably from about 0.5-10 wt-%. The concentration in a semi-solid or solid composition such as a gel or a powder will be about 0.1-5 wt-%, preferably about 0.5-2.5 wt-%.

The amount of the compound or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 1.0 to about 100 mg/kg, preferably from about 10 to about 75 mg/kg of body weight per day, more preferably 5 to about 20 mg per kilogram body weight of the recipient per day.

The compound can be conveniently administered in unit dosage form; for example, tablets, caplets, etc., containing 4 to 400 mg, preferably 10 to 200 mg, most preferably, 20 to 100 mg of active ingredient per unit dosage form.

Ideally, the active ingredient should be administered to achieve peak plasma concentrations of the active compound of from about 0.02 to about 20 µM, preferably, about 0.1 to 10 µM, most preferably, about 0.5 to about 5 µM. These concentrations may be achieved, for example, by the intravenous injection of a 0.005 to 0.5% solution of the active ingredient, or orally administered as a bolus containing about 4 to 400 mg of the active ingredient.

The compounds of the invention can be administered by inhalation from an inhaler, insufflator, atomizer or pressurized pack or other means of delivering an aerosol spray. Pressurized packs may comprise a suitable propellant such as carbon dioxide or other suitable gas. In case of a pressurized aerosol, the dosage unit may be determined by providing a value to deliver a metered amount. The inhalers, insufflators, atomizers are fully described in pharmaceutical reference books such as Remington's Pharmaceutical Sciences Editions 16 (1980) or 18 (1990), Mack Publishing Co.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

All patents, patent applications, books and literature cited in the specification are hereby incorporated by reference in their entirety. In the case of any inconsistencies, the present disclosure, including any definitions therein will prevail. The invention has been described with reference to various specific and preferred embodiments and techniques. However, it should be understood that many variations and modifications may be made while remaining within the spirit and scope of the invention.

The invention will now be illustrated by the following non-limiting Examples.

EXAMPLES

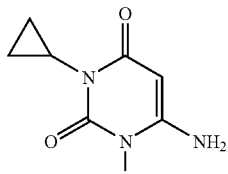

2

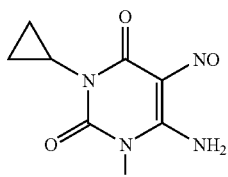

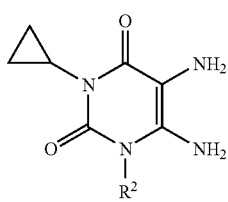

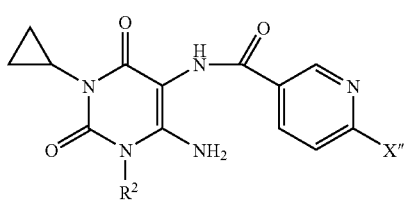

8

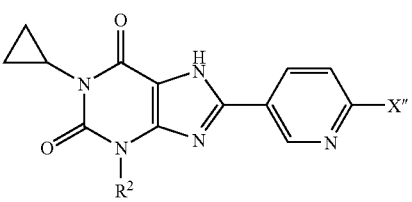

9

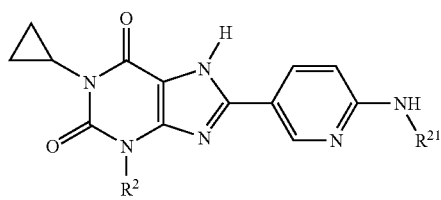

10

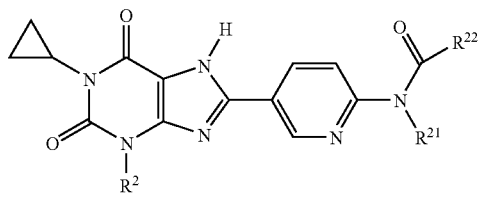

Wherein $R^2$ is hydrogen, or is selected from the group consisting of substituted or unsubstituted $(C_{1-8})$alkyl, halo $(C_{1-8})$alkyl, $(C_{3-8})$alkenyl, $(C_{3-8})$alkenyl$(C_{1-8})$alkyl, $(C_{3-8})$ alkynyl, $(C_{3-8})$alkynyl$(C_{1-8})$alkyl, $(C_{1-8})$alkoxy, $(C_{3-8})$cycloalkyl, $(C_{3-8})$cycloalkyl$(C_{1-8})$alkyl-, $(C_{4-10})$heterocyclyl, $(C_{4-10})$heterocyclyl$(C_{1-8})$alkyl-, $(C_{6-10})$aryl, $(C_{6-10})$aryloxy, $(C_{6-10})$aryl$(C_{1-8})$alkyl-, $(C_{5-10})$heteroaryl and $(C_{5-10})$heteroaryl$(C_{1-8})$alkyl-; $R^{21}$ and $R^{22}$ are each independently selected from the group consisting of hydrogen, or substituted or unsubstituted perhalo$(C_{1-8})$alkyl, amino, $(C_{1-8})$alkyl, $(C_{2-8})$alkene, $(C_{2-8})$alkyne, $(C_{3-12})$cycloalkyl, heterocycloalkyl, aryl$(C_{1-8})$alkyl, heteroaryl, $(C_{9-12})$bicycloaryl, hetero$(C_{8-12})$bicycloaryl, carbonyl group, thiocarbonyl, aryl, heteroaryl, $(C_{1-8})$alkoxy, aryloxy, heteroaryloxy; and X" is Br, Cl or I; or their pharmaceutically acceptable salt thereof.

Pharmacology:

The ability of compounds of the invention to act as an $A_{2B}$ adenosine receptor antagonists may be determined using pharmacological models which are well known to the art or using test procedures described below.

The rat $A_{2B}$ receptor cDNA was subcloned into the expression plasmid pDoubleTrouble using techniques described in Robeva, A. et al., *Biochem. Pharmacol.*, 51, 545-555 (1996). The plasmid was amplified in competent JM109 cells and plasmid DNA isolated using Wizard Megaprep columns (Promega Corporation, Madison, Wis.). $A_{2B}$ adenosine receptors were introduced into HEK-293 cells by means of Lipofectin as described in Felgner, P. L. et al., *Proc. Natl. Acad. Sci. USA,* 84, 7413-7417 (1987).

Cell Culture

Transfected HEK cells were grown under 5% $CO_2$/95% $O_2$ humidified atmosphere at a temperature of 37° C. Colonies were selected by growth of cells in 0.6 mg/mL G418. Transfected cells were maintained in DMEM supplemented with Hams F12 nutrient mixture (1/1), 10% newborn calf serum, 2 mM glutamine and containing 50 IU/mL penicillin, 50 mg/mL streptomycin, and 0.2 mg/mL Geneticin (G418, Boehringer Mannheim). Cells were cultured in 10 cm diameter round plates and subcultured when grown confluent (approximately after 72 hours).

Radioligand Binding Studies

At $A_{2B}$ receptors: Confluent monolayers of HEK-$A_{2B}$ cells were washed with PBS followed by ice cold Buffer A (10 mM HEPES, 10 mM EDTA, pH 7.4) with protease inhibitors (10 µg/mL benzamidine, 100 µM phenylmethanesulfonyl fluoride, and 2 µg/mL of each aprotinin, pepstatin and leupeptin). The cells were homogenized in a Polytron (Brinkmann) for 20 s, centrifuged at 30,000×g, and the pellets washed twice with buffer HE (10 mM HEPES, 1 mM EDTA, pH 7.4 with protease inhibitors). The final pellet was resuspended in buffer HE, supplemented with 10% sucrose and frozen in aliquots at −80° C. For binding assays membranes were thawed and diluted 5-10 fold with HE to a final protein concentration of approximately 1 mg/mL. To determine protein concentrations, membranes, and bovine serum albumin standards were dissolved in 0.2% NaOH/0.01% SDS and protein determined using fluorescamine fluorescence. Stowell, C. P. et al., *Anal. Biochem.*, 85, 572-580 (1978).

Saturation binding assays for rat $A_{2B}$ adenosine receptors were performed with [$^3$H]ZM214,385 (17 Ci/mmol, Tocris Cookson, Bristol UK) (Ji, X. et al., *Drug Design Discov.*, 16, 216-226 (1999)) or $^{125}$I-ABOPX (2200 Ci/mmol). To prepare $^{125}$I-ABOPX, 10 µL of 1 mM ABOPX in methanol/1 M NaOH (20:1) was added to 50 µL of 100 mM phosphate buffer, pH 7.3. One or 2 mCi of Na$^{125}$I was added, followed by 10 µL of 1 mg/mL chloramine-T in water. After incubation, 20 minutes at room temperature, 50 µL of 10 mg/mL Na-metabisulfite in water was added to quench the reaction.

The reaction mixture was applied to a C18 HPLC column, eluting with a mixture of methanol and 5 mM phosphate, pH 6.0. After 5 min at 35% methanol, the methanol concentration was ramped to 100% over 15 min. Unreacted ABOPX eluted in 11-12 minutes; $^{125}$I-ABOPX eluted at 18-19 min in a yield of 50-60% with respect to the initial $^{125}$I.

In equilibrium binding assays the ratio of $^{127}$I/$^{125}$I-ABOPX was 10-20/1. Radioligand binding experiments were performed in triplicate with 20-25 µg membrane protein in a total volume of 0.1 mL HE buffer supplemented with 1 U/mL adenosine deaminase and 5 mM $MgCl_2$. The incubation time was 3 h at 21° C. Nonspecific binding was measured in the presence of 100 µM NECA. Competition experiments were carried out using 0.6 nM $^{125}$I-ABOPX. Membranes were filtered on Whatman GF/C filters using a Brandel cell harvester (Gaithersburg, Md.) and washed 3 times over 15-20 seconds with ice cold buffer (10 mM Tris, 1 mM $MgCl_2$, pH 7.4). $B_{max}$ and $K_D$ values were calculated by Marquardt's nonlinear least squares interpolation for single a site binding models. Marquardt, D. M., *J. Soc. Indust. Appl. Math.*, 11, 431-441.21 (1963). $K_i$ values for different compounds were derived from $IC_{50}$ values as described. Linden, J., *J. Cycl. Nucl. Res.*, 8, 163-172 (1982). Data from replicate experiments are tabulated as means ± SEM.

At other Adenosine Receptors: [$^3$H]CPX. Bruns, R. F. et al., *Naunyn-Schmiedeberg's Arch. Pharmacol.*, 335, 59-63 (1987). $^{125}$I-ZM241385 and $^{125}$I-ABA were utilized in radioligand binding assays to membranes derived from HEK-293 cells expressing recombinant rat $A_1$, $A_{2A}$ and $A_3$ ARs, respectively. Binding of [$^3$H]R-N$^6$-phenylisopropyladenosine. Schwabe, U. et al., *Naunyn-Schmiedeberg's Arch. Pharmacol.*, 313, 179-187 (1980). ([$^3$H]R-PIA, Amersham, Chicago, Ill.) to $A_1$ receptors from rat cerebral cortical membranes and of [$^3$H]CGS 21680. Jarvis, M. F. et al., *J. Pharmacol. Exp. Therap.*, 251, 888-893 (1989). (Dupont NEN, Boston, Mass.) to $A_{2A}$ receptors from rat striatal membranes was performed as described. Adenosine deaminase (3 units/mL) was present during the preparation of the brain membranes, in a preincubation of 30 min at 30° C., and during the incubation with the radioligands. All non-radioactive compounds were initially dissolved in DMSO, and diluted with buffer to the final concentration, where the amount of DMSO never exceeded 2%. Incubations were terminated by rapid filtration over Whatman GF/B filters, using a Brandell cell harvester (Brandell, Gaithersburg, Md.). The tubes were rinsed three times with 3 mL buffer each.

At least six different concentrations of competitor, spanning 3 orders of magnitude adjusted appropriately for the $IC_{50}$ of each compound, were used. $IC_{50}$ values, calculated with the nonlinear regression method implemented in (Graph-Pad Prism, San Diego, Calif.), were converted to apparent Ki values as described. Linden, J., *J. Cycl. Nucl. Res.*, 8:163-172 (1982). Hill coefficients of the tested compounds were in the range of 0.8 to 1.1.

Functional Assay:

HEK-$A_{2B}$ cells from one confluent T75 flask were rinsed with $Ca^{2+}$ and $Mg^{2+}$—free Dulbecco's phosphate buffered saline (PBS) and then incubated in $Ca^{2+}$ and $Mg^{2+}$—free HBSS with 0.05% trypsin and 0.53 mM EDTA until the cells detached. The cells were rinsed twice by centrifugation at 250×g in PBS and resuspended in 10 mL of HBSS composed of 137 mM NaCl, 5 mM KCl, 0.9 mM $MgSO_4$, 1.4 mM $CaCl_2$, 3 mM $NaHCO_3$, 0.6 mM $Na_2HPO_4$, 0.4 mM $KH_2PO_4$, 5.6 mM glucose, and 10 mM HEPES, pH 7.4 and the $Ca^{2+}$-sensitive fluorescent dye indo-1-AM (5 µM) 37° C. for 60 min. The cells were rinsed once and resuspended in 25 mL dye-free HBSS supplemented with 1 U/ml adenosine deaminase and held at room temperature. Adenosine receptor antagonists prepared as 100× stocks in DMSO or vehicle was added and the cells and transferred to a 37° C. bath for 2 minutes. Then the cells (1 million in 2 ml) were transferred to a stirred cuvette maintained at 37° C. within an Aminco SLM 8000 spectrofluorometer (SML instruments, Urbana Ill.). The ratios of indo-1 fluorescence obtained at 400 and 485 nm (excitation, 332 nm) was recorded using a slit width of 4 nm. NECA was added after a 100 s equilibration period.

Cyclic AMP Accumulation

Cyclic AMP generation was performed in DMEM/HEPES buffer (DMEM containing 50 mM HEPES, pH 7.4, 37° C.). Each well of cells was washed twice with DMEMIHEPES buffer, and then 100 µL adenosine deaminase (final concentration 10 IU/mL) and 100 µL of solutions of rolipram and cilostamide (each at a final concentration of 10 µM) were added, followed by 50 µL of the test compound (appropriate concentration) or buffer. After 15 minutes, incubation at 37° C. was terminated by removing the medium and adding 200 µL of 0.1 M HCl. Acid extracts were stored at −20° C. until assay. The amounts of cyclic AMP were determined following a protocol which utilized a cAMP binding protein (PKA) [van der Wenden et al., 1995], with the following minor modifications. The assay buffer consisted of 150 mM $K_2HPO_4$/10 mM EDTA/0.2% BSA FV at pH 7.5. Samples (20 mL) were incubated for 90 minutes at 0° C. Incubates were filtered over GF/C glass microfiber filters in a Brandel M-24 Cell Harvester. The filters were additionally rinsed with 4 times 2 mL 150 mM $K_2HPO_4$/10 mM EDTA (pH 7.5, 4° C.). Punched filters were counted in Packard Emulsifier Safe scintillation fluid after 2 hours of extraction.

Available data from the affinity testing for the compounds of the invention are reported in Table 1. The data reported for the $A_{2B}$ term is the level of displacement of specific [$^{125}$I] ABOPX binding at rat $A_{2B}$ receptors ($rA_{2B}$) expressed in HEK-293 cells.

Synthesis and Characterization

Proton nuclear magnetic resonance spectroscopy was performed on a Varian-300 MHz spectrometer and spectra were taken in DMSO-$d_6$ or $CDCl_3$. Unless noted, chemical shifts are expressed as ppm downfield from tetramethylsilane or relative ppm from DMSO (2.5 ppm). Electro-spray-ionization (ESI) mass spectrometry was performed with a ThermoFinnigan LCQ mass spectrometer.

All xanthine derivatives were homogeneous as judged using TLC (Silica gel 60 $F_{254}$, 0.25 mm, aluminium backed, EM Science, Gibbstown, N.J.) and HPLC (Shimadzu) using Varian C18 5 micron analytical column (4.6 mm×150 mm) in linear gradient or isocratic solvent system, at a flow rate of 1 ml /min. The solvent system used was MeOH (0.1% formic acid):$H_2O$ (0.1% formic acid). Peaks were detected by UV absorption at 232 nm and 254 nm. NMR and mass spectra were shown to be consistent with the assigned structure.

EXAMPLES

The following compounds of the invention are prepared using the procedures described herein-above:

Preparation of N-cyclopropyl, N'-propylurea (1):

Cyclopropylamine (5.7 g, 0.1 mole) in toluene (50 ml) was cooled with an ice-bath. N-propyl isocyanate (8.5 g, 0.1 mole) was added dropwise to the cooled cyclopropylamine solution. The mixture was stirred at 4° C. for 2 h and then at room temperature for another 2 h. The precipitate was filtered and dried to give N-cyclopropyl, N'-propylurea (1) (10 g, 70%).

Preparation of 1-propyl, 3-cyclopropyl, 6-aminouracil (2):

N-cyclopropyl, N'-propylurea (1) (14.2 g, 0.1 mole), cyanoacetic acid (9.35 g, 0.11 mole) and acetic anhydride (35 ml) were mixture together and heated at 80° C. for 2 h. The solvent was then removed under reduced pressure. The residue was dissolved in MeOH (30 ml) and 20% NaOH (10 ml) was added at 4° C. The mixture was stirred at 4° C. for 1 h and then at room temperature for another 20 min. The solvent was then removed under reduced pressure and the residue was purified by silica gel column chromatography as well as C-18 column chromatography to give pure 1-propyl, 3-cyclopropyl, 6-aminouracil (2) (5.23 g, 25%).

Preparation of 1-propyl, 3-cyclopropyl, 6-amino, 5-nitrosouracil (4):

1-Propyl, 3-cyclopropyl, 6-aminouracil (2) (12.8 g, 61.2 mmol) was dissolved in acetic acid (25 ml) in 200 ml of water and the mixture was cooled to 10° C. To the uracil solution, NaNO$_2$ (7.6 g, 110.1 mmol) in 50 ml of water was added dropwise at 10° C. The mixture was stirred at 10° C. for 30 min and then at room temperature for 1 h. The solvent was removed under reduced pressure and the residue was dissolved in the mixture of absolute ethanol and CH$_2$Cl$_2$ (1:1) and boiled for 20 min. The hot mixture was filtered through a layer of Celite 545 to remove the insoluble inorganic salts. The mother liquid was evaporated under reduced pressured to remove the solvent to give 1-propyl, 3-cyclopropyl, 6-amino, 5-nitrosouracil (4) (11.4 g, 78%).

Preparation of 1-propyl, 3-cyclopropyl, 5,6-diaminouracil (5):

1-Propyl, 3-cyclopropyl, 6-amino, 5-nitrosouracil (4) (4.0 g, 17.33 mmol) was dissolved in absolute ethanol (30 ml) in a hydrogenation flask. 10% Pd/C (400 mg) was added and the flask was purged with hydrogen. The mixture was stirred under nitrogen until the intake of hydrogen complete. The mixture was filtered through a layer of Celite 545. The mother liquid was evaporated under reduced pressured and dried under vacuum to give 1-propyl-3-cyclopropyl-5,6-diaminouracil (5) (3.9 g, 100%). Compound 5 was used in the next step without further purification.

Preparation of 1-cyclopropyl, 3-propyl-8-(6-chloro-3-pyridyl)xanthine (8):

6-Chloronicotinoyl chloride (1.83 g, 10.4 mmol), in CH$_2$Cl$_2$ (20 ml) was added dropwise to a solution of 1-propyl-3-cyclopropyl-5,6-diamino-uracil (1.808 g, 8 mmol) in dry pyridine (8.2 ml) maintained at 5° C. The reaction was warmed to room temperature and stirred for an additional 3 hours. Water (50 ml) was added to quench the reaction. The solvent was evaporated to afford a dark colored oil. The oil was refluxed for 2 h in 2N NaOH (20 ml). After cooling, the pH was carefully adjusted to 7 with concentrated HCl. A solid formed and was collected and washed with water (20 ml), ether (20 ml) and chloroform (20 ml) to provide an off-white solid (1.9 g). The product was used in the next step without further purification.

General procedures for the reaction of 1-cyclopropyl, 3-propyl-8-(6-chloro-3-pyridyl)xanthine (8) with substituted amines.

Compound 8 (4 g, 11.5 mmol) and the corresponding substituted amine (6-10 equivalents) were put in a pressure tube. Ethanol (50 ml) was added. The pressure tube was flushed with argon, sealed and stirred at 160° C. for 48-60 h. After cooling, ether (10 ml) was added. The resulting solid was collected and purified by silica gel column (Solvent A: CH$_2$Cl$_2$:MeOH=20:1 to 10:1 or Solvent B:CH$_2$Cl$_2$:MeOH:TEA=20:1:0.1 to 4:1:0.1) to give compound 9.

General Procedures for the Preparation of Amide Compounds (10):

The amino substituted pyridyl compound (50 mg) was dissolved in dry pyridine (25 ml). The desired acid chloride (4-6 equivalents) was added at room temperature. The mixture was stirred at room temperature for 24-60 h. The solvent was removed and the residue was purified by silica gel column or preparative TLC (CH$_2$Cl$_2$:MeOH=110:10 or Ethyl Acetate:Hexane:MeOH=15:85:5) to give compound 10.

What is claimed is:

1. A process for preparing a compound of formula VII:

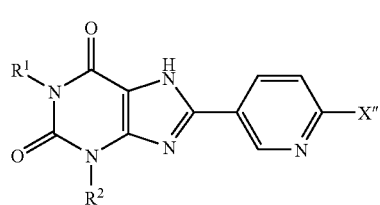

the process, comprising:

(a) contacting a 5,6-diamino-1H-pyrimidine-2,4-dione of formula II:

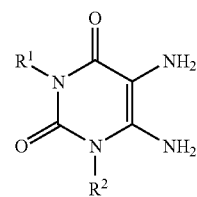

with an acylating agent of formula VI:

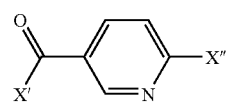

in an aprotic solvent to produce a 1H-pryimidine-2,4-dione of formula IV:

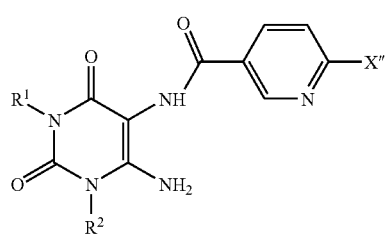

(b) contacting the 1H-pryimidine-2,4-dione of formula IV with a base to produce a xanthine of formula VII;

wherein:

X' and X" are each independently selected from the group consisting of Cl, Br, and I;

R$^1$ is (C$_{3-8}$)cycloalkyl; and, $R^2$ is hydrogen, or is selected from the group consisting of substituted or unsubstituted $(C_{1-8})$alkyl, halo$(C_{1-8})$alkyl-, $(C_{3-8})$alkenyl, $(C_{3-8})$alkenyl$(C_{1-8})$alkyl-, $(C_{3-8})$alkynyl, $(C_{3-8})$alkynyl$(C_{1-8})$alkyl-, $(C_{1-8})$alkoxy, $(C_{3-8})$cycloalkyl, $(C_{3-8})$cycloalkyl$(C_{1-8})$alkyl-, $(C_{4-10})$hererocyclyl, $(C_{4-10})$heterocyclyl$(C_{1-8})$alkyl-, $(C_{6-10})$aryl, $(C_{6-10})$aryloxy, $(C_{6-10})$aryl$(C_{1-8})$alkyl-, $(C_{5-10})$heteroaryl, and $(C_{5-10})$heteroaryl$(C_{1-8})$alkyl-.

2. The process of claim 1, wherein the acylating agent is further selected from the group consisting of:

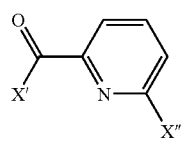
VIa

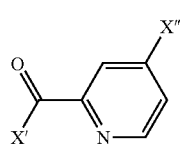
VIb

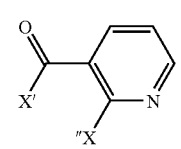
VIc

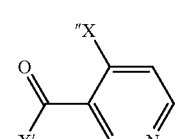
VId

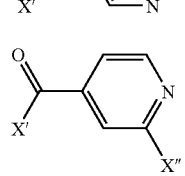
VIe and the resulting xanthine products formed are selected from the group consisting of VIIa-VIIe;

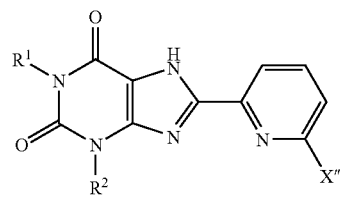
VIIa

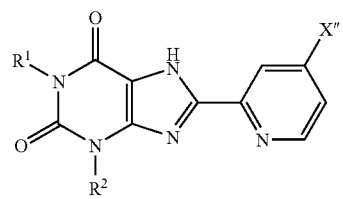
VIIb

-continued

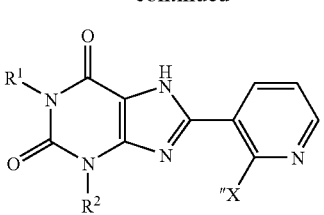
VIIc

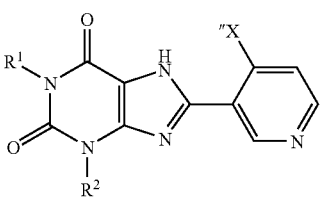
VIId

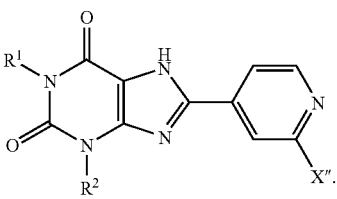
VIIe

3. The process of claim 1, wherein a compound of the formulae VII and VIIa-VIIe is further contacted with an amine of the formula R'—NH$_2$ to produce a compound of the formula VIII-VIIIe;

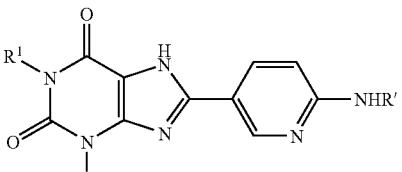
VIII

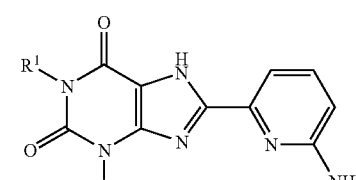
VIIIa

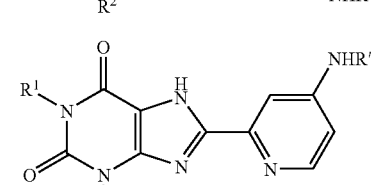
VIIIb

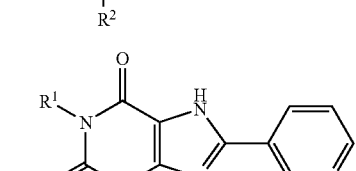
VIIIc

-continued

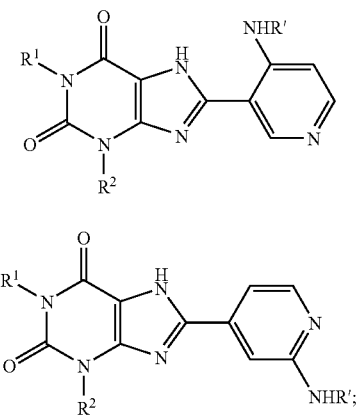

VIIId

VIIIe which is further contacted with a compound of the formula Z¹C(O)—W to form a compound of the formula IX-IXe:

IX

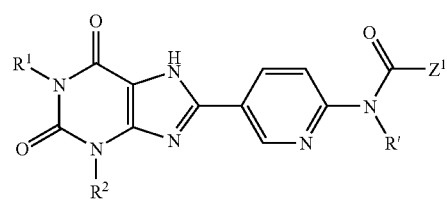

IXa

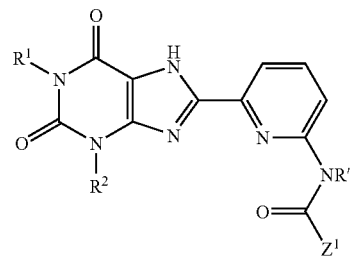

IXb

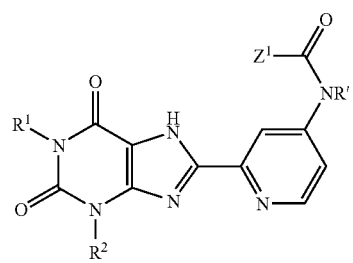

IXc

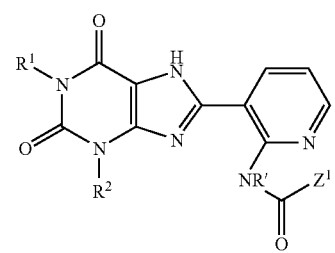

-continued

IXd

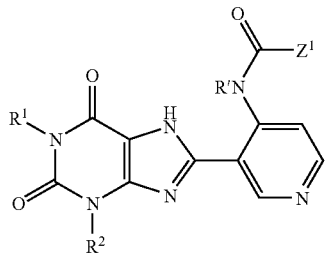

IXe

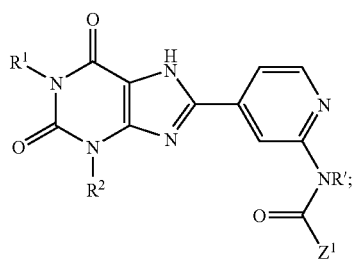

wherein:

W is a leaving group;

R' is selected from the group consisting of amino, $(C_{1-4})$ alkyl, halo$(C_{1-4})$alkyl, $(C_{3-8})$alkenyl, $(C_{3-8})$alkynyl, $(C_{1-4})$alkoxy$(C_{1-4})$alkyl-, $R^4R^5N(C_{1-4})$alkyl-, $R^4R^5NC(O)(C_{1-4})$alkyl-, $(C_{3-6})$cycloalkyl, $(C_{3-6})$cycloalkyl$(C_{1-4})$alkyl-, $(C_{4-10})$heterocyclyl$(C_{1-4})$alkyl-, $(C_{6-10})$aryl$(C_{1-4})$alkyl-, and $(C_{5-10})$heteroaryl$(C_{1-8})$alkyl-, each substituted or unsubstituted;

$R^1$ is $(C_{3-8})$cycloalkyl;

$R^2$ is hydrogen, or is selected from the group consisting of substituted or unsubstituted $(C_{1-8})$alkyl, halo$(C_{1-8})$alkyl, $(C_{3-8})$alkenyl, $(C_{3-8})$alkenyl$(C_{1-8})$alkyl-, $(C_{3-8})$alkynyl, $(C_{3-8})$alkynyl$(C_{1-8})$alkyl-, $(C_{1-8})$alkoxy, $(C_{3-8})$cycloalkyl, $(C_{3-8})$cycloalkyl$(C_{1-8})$alkyl-, $(C_{4-10})$heterocyclyl, $(C_{4-10})$heterocyclyl$(C_{1-8})$alkyl-, $(C_{6-10})$aryl, $(C_{6-10})$aryloxy, $(C_{6-10})$aryl$(C_{1-8})$alkyl-, $(C_{5-10})$heteroaryl, and $(C_{5-10})$heteroaryl$(C_{1-8})$alkyl-;

$Z^1$ is a 5-14 member substituted or unsubstituted monocyclic aryl, polycyclic aryl, or heteroaryl ring; and, $R^4$ and $R^5$ each are independently hydrogen or are selected from the group consisting of $(C_{1-8})$alkyl, $(C_{3-8})$alkenyl, $(C_{3-8})$alkynyl, $(C_{1-8})$alkoxy, $(C_{3-8})$cycloalkyl, $(C_{3-8})$cycloalkyl$(C_{1-8})$alkyl-, $(C_{6-18})$polycycloalkyl, $(C_{6-18})$polycycloalkyl$(C_{1-8})$alkyl-, $(C_{3-10})$heterocyclyl, $(C_{3-10})$heterocyclyl$(C_{1-8})$alkyl-, $((C_{1-8})$alkyl$)_2$N—$(C_{6-10})$aryl-, $(C_{6-10})$aryl$(C_{1-8})$alkyl-, $(C_{5-10})$heteroaryl, $(C_{5-10})$heteroaryl$(C_{1-8})$alkyl-, $(C_{1-8})$alkyl)C(O)—, $(C_{1-8})$alkyCO$_2$—, —C(O)N($(C_{1-8})$alkyl$)_2$, —S(O)$(C_{1-8})$alkyl, —S(O)N($(C_{1-8})$alkyl$)_2$, —S(O)$_2$$(C_{1-8})$alkyl, and —S(O)$_2$N($(C_{1-8})$alkyl$)_2$.

4. The process of claim 2, wherein a compound of formula VII-VIIe is further contacted with an amine of the formula R'—NHC(O)Z¹ at an elevated temperature to produce a compound of the formula IX-IXe:

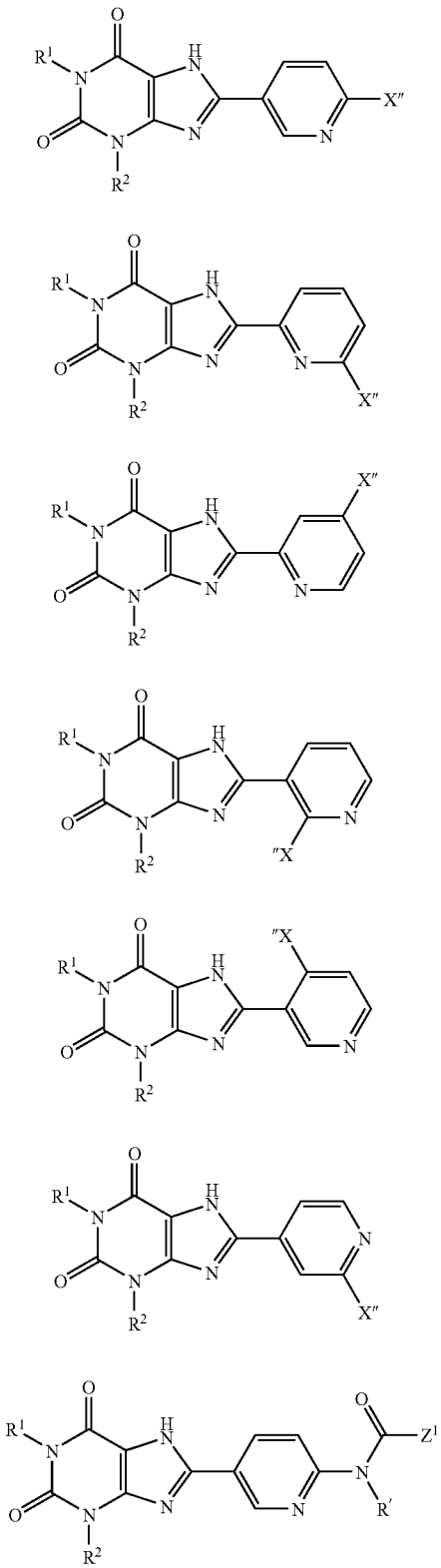

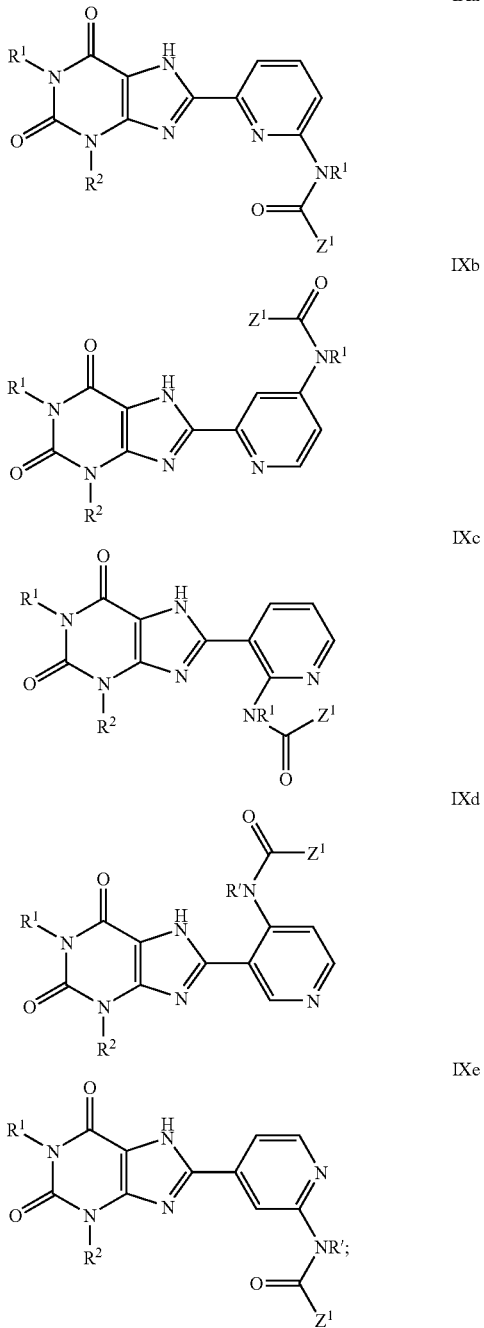

wherein:

R' is selected from the group consisting of amino, $(C_{1-4})$ alkyl, halo$(C_{1-4})$alkyl, $(C_{3-8})$alkenyl, $(C_{3-8})$alkynyl, $(C_{1-4})$alkoxy$(C_{1-4})alkyl$-, $R^4R^5N(C_{1-4})$alkyl-, $R^4R^5NC(O)(C_{1-4})$alkyl-, $(C_{3-6})$cycloalkyl, $(C_{3-6})$cycloalkyl$(C_{1-4})$alkyl-, $(C_{4-10})$heterocyclyl$(C_{1-4})$alkyl-, $(C_{6-10})$aryl$(C_{1-4})$alkyl- and $(C_{5-10})$heteroaryl$(C_{1-8})$alkyl-, each substituted or unsubstituted;

$Z^1$ is a 5-14 member substituted or unsubstituted monocyclic aryl, polycyclic aryl, or heteroaryl ring; and $R^4$ and $R^5$ each are independently selected from the group consisting of hydrogen, $(C_{1-8})$alkyl, $(C_{3-8})$alkenyl, ($C_{3-8}$)alkynyl, ($C_{1-8}$)alkoxy, ($C_{3-8}$)cycloalkyl, ($C_{3-8}$)cycloalkyl($C_{1-8}$)alkyl-, ($C_{6-18}$)polycycloalkyl, ($C_{6-8}$)polycycloalkyl($C_{1-8}$)alkyl-, ($C_{3-10}$)heterocyclyl, ($C_{3-10}$)heterocyclyl($C_{1-8}$)alkyl-, (($C_{1-8}$)alkyl)$_2$N—($C_{6-10}$)aryl-, ($C_{6-10}$)aryl($C_{1-8}$)alkyl-, ($C_{5-10}$)heteroaryl, ($C_{5-10}$)heteroaryl($C_{1-8}$)alkyl-, ($C_{1-8}$)alkylC(O)—, ($C_{1-8}$)alkyl CO$_2$—, —C(O)N(($C_{1-8}$)alkyl)$_2$, —S(O)($C_{1-8}$)alkyl, —S(O)N(($C_{1-8}$)alkyl)$_2$, —S(O)$_2$($C_{1-8}$)alkyl, and —S(O)$_2$N(($C_{1-8}$)alkyl)$_2$.

5. The process of claim 1, wherein the elevated temperature is between about 75 and about 185° C.

6. The process of claim 1, wherein the aprotic solvent is an amine.

7. The process of claim 1, wherein the aprotic solvent is a mixture of dichloromethane and pyridine.

8. The process of claim 1, wherein the base is a metal hydroxide selected from the group consisting of lithium hydroxide, calcium hydroxide, sodium hydroxide, potassium hydroxide, and mixtures thereof.

9. The process of claim 8, wherein the base is sodium hydroxide.

10. The process of claim 1, wherein the 1H-pyrimidine-2,4-dione of formula IV is prepared and is converted to the xanthine of the formula V without further purification.

* * * * *

UNITED STATES PATENT AND TRADEMARK OFFICE
CERTIFICATE OF CORRECTION

| | | |
|---|---|---|
| PATENT NO. | : 7,598,379 B2 | Page 1 of 1 |
| APPLICATION NO. | : 11/362390 | |
| DATED | : October 6, 2009 | |
| INVENTOR(S) | : Wang et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 652 days.

Signed and Sealed this

Twenty-eighth Day of September, 2010

David J. Kappos
*Director of the United States Patent and Trademark Office*